United States Patent
Han et al.

(10) Patent No.: US 10,537,449 B2
(45) Date of Patent: Jan. 21, 2020

(54) CONTROLLING POWERED HUMAN AUGMENTATION DEVICES

(71) Applicant: BIONX MEDICAL TECHNOLOGIES, INC., Bedford, MA (US)

(72) Inventors: Zhixiu Han, Acton, MA (US); Christopher Eric Barnhart, Carlisle, MA (US); David Adams Garlow, Sanbornville, NH (US); Adrienne Bolger, Cambridge, MA (US); Hugh Miller Herr, Somerville, MA (US); Gary Girzon, Sudbury, MA (US); Richard J. Casler, Lowell, MA (US); Jennifer T. McCarthy, Concord, MA (US)

(73) Assignee: Bionx Medical Technologies, Inc., Bedford, MA (US)

( * ) Notice: Subject to any disclaimer, the term of this patent is extended or adjusted under 35 U.S.C. 154(b) by 0 days.

(21) Appl. No.: 14/090,359

(22) Filed: Nov. 26, 2013

(65) Prior Publication Data
US 2014/0088727 A1 Mar. 27, 2014

Related U.S. Application Data

(63) Continuation of application No. 13/349,216, filed on Jan. 12, 2012, now abandoned.
(Continued)

(51) Int. Cl.
*A61F 2/68* (2006.01)
*A61F 2/60* (2006.01)
(Continued)

(52) U.S. Cl.
CPC .............. *A61F 2/68* (2013.01); *A61F 2/60* (2013.01); *A61F 2/66* (2013.01); *A61F 2002/7625* (2013.01)

(58) Field of Classification Search
CPC .............. A61F 2/68; A61F 2002/704; A61F 2002/7625; A61F 2002/7635;
(Continued)

(56) References Cited

U.S. PATENT DOCUMENTS 2,489,291 A  11/1949  Henschke et al.
2,529,968 A  11/1950  Sartin
(Continued)

FOREIGN PATENT DOCUMENTS

EP    1393866      3/2004
WO    WO-2003068453  8/2003
(Continued)

OTHER PUBLICATIONS

Thompson, Dave. Energy and Power During the Gait Cycle. Mar. 20, 2002.*
(Continued)

*Primary Examiner* — Christie L Bahena

(57) ABSTRACT

In a communication system for controlling a powered human augmentation device, a parameter of the powered device is adjusted within a gait cycle by wirelessly transmitting a control signal thereto, whereby the adjusted parameter falls within a target range corresponding to that parameter. The target range is selected and the device parameters are controlled such that the powered device can normalize or augment human biomechanical function, responsive to a wearer's activity, regardless of speed and terrain and, in effect, provides at least a biomimetic response to the wearer of the powered device.

15 Claims, 9 Drawing Sheets

Related U.S. Application Data

(60) Provisional application No. 61/432,093, filed on Jan. 12, 2011.

(51) Int. Cl.
   *A61F 2/66* (2006.01)
   *A61F 2/76* (2006.01)

(58) Field of Classification Search
   CPC ...... A61F 2002/7645; A61F 2/60; A61F 2/66; B25J 9/0006
   USPC .............................................. 623/24, 27, 53
   See application file for complete search history.

(56) References Cited

U.S. PATENT DOCUMENTS

| | | |
|---|---|---|
| 3,098,645 A | 7/1963 | Owens |
| 3,207,497 A | 9/1965 | Schoonover |
| 3,844,279 A | 10/1974 | Konvalin |
| 4,442,390 A | 4/1984 | Davis |
| 4,463,291 A | 7/1984 | Usry |
| 4,518,307 A | 5/1985 | Bloch |
| 4,532,462 A | 7/1985 | Washbourn et al. |
| 4,546,295 A | 10/1985 | Wickham et al. |
| 4,546,296 A | 10/1985 | Washbourn et al. |
| 4,546,297 A | 10/1985 | Washbourn et al. |
| 4,546,298 A | 10/1985 | Wickham et al. |
| 4,569,352 A | 2/1986 | Petrofsky et al. |
| 4,600,357 A | 7/1986 | Coules |
| 4,657,470 A | 4/1987 | Clarke et al. |
| 4,843,921 A | 7/1989 | Kremer |
| 4,865,376 A | 9/1989 | Leaver et al. |
| 4,872,803 A | 10/1989 | Asakawa |
| 4,909,535 A | 3/1990 | Clark et al. |
| 4,921,293 A | 5/1990 | Ruoff et al. |
| 4,921,393 A | 5/1990 | Andeen et al. |
| 4,923,474 A | 5/1990 | Klasson et al. |
| 4,923,475 A | 5/1990 | Gosthnian et al. |
| 4,964,402 A | 10/1990 | Grim et al. |
| 4,989,161 A | 1/1991 | Oaki |
| 5,012,591 A | 5/1991 | Asakawa |
| 5,049,797 A | 9/1991 | Phillips |
| 5,062,673 A | 11/1991 | Mimura |
| 5,088,478 A | 2/1992 | Grim |
| 5,092,902 A | 3/1992 | Adams et al. |
| 5,112,295 A | 5/1992 | Beard et al. |
| 5,174,168 A | 12/1992 | Takagi et al. |
| 5,181,933 A | 1/1993 | Phillips |
| 5,252,102 A | 10/1993 | Singer et al. |
| 5,294,873 A | 3/1994 | Seraji |
| RE34,661 E | 7/1994 | Grim |
| 5,327,790 A | 7/1994 | Levin et al. |
| 5,367,790 A | 11/1994 | Garnow et al. |
| 5,383,939 A | 1/1995 | James |
| 5,405,409 A | 4/1995 | Knuth |
| 5,442,270 A | 8/1995 | Tetsuaki |
| 5,443,521 A | 8/1995 | Knoth et al. |
| 5,456,341 A | 10/1995 | Garnjost et al. |
| 5,458,143 A | 10/1995 | Herr |
| 5,476,441 A | 12/1995 | Durfee et al. |
| 5,502,363 A | 3/1996 | Tasch et al. |
| 5,514,185 A | 5/1996 | Phillips |
| 5,556,422 A | 9/1996 | Powell, III et al. |
| 5,571,205 A | 11/1996 | James |
| 5,643,332 A | 7/1997 | Stein |
| 5,650,704 A | 7/1997 | Pratt et al. |
| 5,662,693 A | 9/1997 | Johnson et al. |
| 5,701,686 A | 12/1997 | Herr et al. |
| 5,718,925 A | 2/1998 | Kristinsson et al. |
| 5,748,845 A | 5/1998 | Labun et al. |
| 5,776,205 A | 7/1998 | Phillips |
| 5,885,809 A | 3/1999 | Effenberger et al. |
| 5,888,212 A | 3/1999 | Petrofsky et al. |
| 5,898,948 A | 5/1999 | Kelly et al. |
| 5,910,720 A | 6/1999 | Williamson et al. |
| 5,932,230 A | 8/1999 | DeGrate |
| 5,971,729 A | 10/1999 | Kristinsson et al. |
| 5,972,036 A | 10/1999 | Kristinsson et al. |
| 5,980,435 A | 11/1999 | Joutras et al. |
| 6,029,374 A | 2/2000 | Herr et al. |
| 6,056,712 A | 5/2000 | Grim |
| 6,067,892 A | 5/2000 | Erickson |
| 6,071,313 A | 6/2000 | Phillips |
| 6,136,039 A | 10/2000 | Kristinsson et al. |
| 6,144,385 A | 11/2000 | Girard |
| 6,202,806 B1 | 3/2001 | Sandrin et al. |
| 6,223,648 B1 | 5/2001 | Erickson |
| 6,240,797 B1 | 6/2001 | Morishima et al. |
| 6,267,742 B1 | 7/2001 | Krivosha et al. |
| 6,416,703 B1 | 7/2002 | Kristinsson et al. |
| 6,443,993 B1 | 9/2002 | Koniuk |
| 6,456,884 B1 | 9/2002 | Kenney |
| 6,478,826 B1 | 11/2002 | Phillips et al. |
| 6,485,776 B2 | 11/2002 | Janusson et al. |
| 6,507,757 B1 | 1/2003 | Swain et al. |
| 6,511,512 B2 | 1/2003 | Phillips et al. |
| 6,517,503 B1 | 2/2003 | Naft et al. |
| 6,589,289 B2 | 7/2003 | Ingimarsson |
| 6,592,539 B1 | 7/2003 | Einarsson et al. |
| 6,610,101 B2 | 8/2003 | Herr et al. |
| 6,626,952 B2 | 9/2003 | Janusson et al. |
| 6,666,796 B1 | 12/2003 | MacCready, Jr. |
| 6,706,364 B2 | 3/2004 | Janusson et al. |
| 6,752,774 B2 | 6/2004 | Townsend et al. |
| 6,764,520 B2 | 7/2004 | Deffenbaugh et al. |
| 6,811,571 B1 | 11/2004 | Phillips |
| D503,480 S | 3/2005 | Ingimundarson et al. |
| D503,802 S | 4/2005 | Bjarnason |
| 6,887,279 B2 | 5/2005 | Phillips et al. |
| 6,923,834 B2 | 8/2005 | Karason |
| 6,936,073 B2 | 8/2005 | Karason |
| 6,945,947 B2 | 9/2005 | Ingimundarson et al. |
| 6,966,882 B2 | 11/2005 | Horst |
| 6,969,408 B2 | 11/2005 | Lecomte et al. |
| 6,992,455 B2 | 1/2006 | Kato et al. |
| 7,001,563 B2 | 2/2006 | Janusson et al. |
| 7,025,793 B2 | 4/2006 | Egilsson |
| 7,029,500 B2 | 4/2006 | Martin |
| 7,037,283 B2 | 5/2006 | Karason et al. |
| D523,149 S | 6/2006 | Bjarnason |
| 7,063,727 B2 | 6/2006 | Phillips et al. |
| 7,077,818 B2 | 7/2006 | Ingimundarson et al. |
| 7,094,058 B2 | 8/2006 | Einarsson |
| 7,094,212 B2 | 8/2006 | Karason et al. |
| D527,825 S | 9/2006 | Ingimundarson et al. |
| D529,180 S | 9/2006 | Ingimundarson et al. |
| 7,101,487 B2 | 9/2006 | Hsu et al. |
| 7,105,122 B2 | 9/2006 | Karason |
| 7,107,180 B2 | 9/2006 | Karason |
| 7,118,601 B2 | 10/2006 | Yasui et al. |
| 7,118,602 B2 | 10/2006 | Bjarnason |
| 7,136,722 B2 | 11/2006 | Nakamura et al. |
| D533,280 S | 12/2006 | Wyatt et al. |
| 7,144,429 B2 | 12/2006 | Carstens |
| 7,145,305 B2 | 12/2006 | Takenaka et al. |
| 7,154,017 B2 | 12/2006 | Sigurjonsson et al. |
| 7,161,056 B2 | 1/2007 | Gudnason et al. |
| 7,169,188 B2 | 1/2007 | Carstens |
| 7,169,189 B2 | 1/2007 | Bjarnason et al. |
| 7,169,190 B2 | 1/2007 | Phillips et al. |
| 7,198,071 B2 | 4/2007 | Bisbee, III et al. |
| 7,198,610 B2 | 4/2007 | Ingimundarson et al. |
| 7,217,060 B2 | 5/2007 | Ingimarsson |
| 7,220,889 B2 | 5/2007 | Sigurjonsson et al. |
| 7,223,899 B2 | 5/2007 | Sigurjonsson |
| 7,227,050 B2 | 6/2007 | Sigurjonsson et al. |
| 7,230,154 B2 | 6/2007 | Sigurjonsson |
| 7,235,108 B2 | 6/2007 | Carstens |
| 7,240,876 B2 | 7/2007 | Doubleday et al. |
| 7,266,910 B2 | 9/2007 | Ingimundarson |
| 7,270,644 B2 | 9/2007 | Ingimundarson |
| 7,279,009 B2 | 10/2007 | Herr et al. |
| 7,288,076 B2 | 10/2007 | Grim et al. |
| 7,295,892 B2 * | 11/2007 | Herr et al. ................ 700/245 |

(56) References Cited

U.S. PATENT DOCUMENTS

| | | |
|---|---|---|
| RE39,961 E | 12/2007 | Petrofsky et al. |
| 7,303,538 B2 | 12/2007 | Grim et al. |
| 7,304,202 B2 | 12/2007 | Sigurjonsson et al. |
| 7,311,686 B1 | 12/2007 | Iglesias et al. |
| 7,313,463 B2 | 12/2007 | Herr et al. |
| D558,884 S | 1/2008 | Ingimundarson et al. |
| 7,335,233 B2 | 2/2008 | Hsu et al. |
| 7,347,877 B2 | 3/2008 | Clausen et al. |
| D567,072 S | 4/2008 | Ingimundarson et al. |
| 7,371,262 B2 | 5/2008 | Lecomte et al. |
| 7,377,944 B2 | 5/2008 | Janusson et al. |
| RE40,363 E | 6/2008 | Grim et al. |
| 7,381,860 B2 | 6/2008 | Gudnason et al. |
| 7,393,364 B2 | 7/2008 | Martin |
| 7,396,975 B2 | 7/2008 | Sigurjonsson et al. |
| 7,402,721 B2 | 7/2008 | Sigurjonsson et al. |
| 7,411,109 B2 | 8/2008 | Sigurjonsson et al. |
| D576,781 S | 9/2008 | Chang et al. |
| D577,828 S | 9/2008 | Ingimundarson et al. |
| 7,423,193 B2 | 9/2008 | Sigurjonsson et al. |
| 7,427,297 B2 | 9/2008 | Patterson et al. |
| 7,429,253 B2 | 9/2008 | Shimada et al. |
| 7,431,708 B2 | 10/2008 | Sreeramagiri |
| 7,431,737 B2 | 10/2008 | Ragnarsdottir et al. |
| 7,438,843 B2 | 10/2008 | Asgeirsson |
| 7,449,005 B2 | 11/2008 | Pickering et al. |
| 7,455,696 B2 | 11/2008 | Bisbee, III et al. |
| D583,956 S | 12/2008 | Chang et al. |
| 7,459,598 B2 | 12/2008 | Sigurjonsson et al. |
| 7,465,281 B2 | 12/2008 | Grim et al. |
| 7,465,283 B2 | 12/2008 | Grim et al. |
| 7,468,471 B2 | 12/2008 | Sigurjonsson et al. |
| 7,470,830 B2 | 12/2008 | Sigurjonsson et al. |
| 7,488,349 B2 | 2/2009 | Einarsson |
| 7,488,864 B2 | 2/2009 | Sigurjonsson et al. |
| D588,753 S | 3/2009 | Ingimundarson et al. |
| 7,503,937 B2 | 3/2009 | Asgeirsson et al. |
| 7,513,880 B2 | 4/2009 | Ingimundarson et al. |
| 7,513,881 B1 | 4/2009 | Grim et al. |
| D592,755 S | 5/2009 | Chang et al. |
| D592,756 S | 5/2009 | Chang et al. |
| 7,531,006 B2 | 5/2009 | Clausen et al. |
| 7,531,711 B2 | 5/2009 | Sigurjonsson et al. |
| 7,534,220 B2 | 5/2009 | Cormier et al. |
| 7,544,214 B2 | 6/2009 | Gramnas |
| 7,549,970 B2 | 6/2009 | Tweardy |
| D596,301 S | 7/2009 | Campos et al. |
| 7,578,799 B2 | 8/2009 | Thorsteinsson et al. |
| 7,581,454 B2 | 9/2009 | Clausen et al. |
| 7,597,672 B2 | 10/2009 | Kruijsen et al. |
| 7,597,674 B2 | 10/2009 | Hu et al. |
| 7,597,675 B2 | 10/2009 | Ingimundarson et al. |
| 7,618,463 B2 | 11/2009 | Oddsson et al. |
| 7,632,315 B2 | 12/2009 | Egilsson |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,650,204 B2 | 1/2010 | Dariush |
| 7,662,191 B2 | 2/2010 | Asgeirsson |
| D611,322 S | 3/2010 | Robertson |
| 7,674,212 B2 | 3/2010 | Kruijsen et al. |
| 7,691,154 B2 | 4/2010 | Asgeirsson et al. |
| 7,696,400 B2 | 4/2010 | Sigurjonsson et al. |
| 7,704,218 B2 | 4/2010 | Einarsson et al. |
| D616,555 S | 5/2010 | Thorgilsdottir et al. |
| D616,556 S | 5/2010 | Hu |
| 7,713,225 B2 | 5/2010 | Ingimundarson et al. |
| D616,996 S | 6/2010 | Thorgilsdottir et al. |
| D616,997 S | 6/2010 | Thorgilsdottir et al. |
| D618,359 S | 6/2010 | Einarsson |
| 7,727,174 B2 | 6/2010 | Chang et al. |
| 7,736,394 B2 | 6/2010 | Bedard et al. |
| 7,745,682 B2 | 6/2010 | Sigurjonsson et al. |
| D620,124 S | 7/2010 | Einarsson |
| 7,749,183 B2 | 7/2010 | Ingimundarson et al. |
| 7,749,281 B2 | 7/2010 | Egilsson |
| 7,762,973 B2 | 7/2010 | Einarsson et al. |
| 7,771,488 B2 | 8/2010 | Asgeirsson et al. |
| 7,780,741 B2 | 8/2010 | Janusson et al. |
| 7,794,418 B2 | 9/2010 | Ingimundarson et al. |
| 7,794,505 B2 | 9/2010 | Clausen et al. |
| 7,811,333 B2 | 10/2010 | Jonsson et al. |
| 7,811,334 B2 | 10/2010 | Ragnarsdottir et al. |
| D627,079 S | 11/2010 | Robertson |
| 7,833,181 B2 | 11/2010 | Cormier et al. |
| 7,842,848 B2 | 11/2010 | Janusson et al. |
| D628,696 S | 12/2010 | Robertson |
| D629,115 S | 12/2010 | Robertson |
| 7,846,213 B2 | 12/2010 | Lecomte et al. |
| 7,862,620 B2 | 1/2011 | Clausen et al. |
| 7,863,797 B2 | 1/2011 | Calley |
| 7,867,182 B2 | 1/2011 | Iglesias et al. |
| 7,867,284 B2 | 1/2011 | Bedard |
| 7,867,285 B2 | 1/2011 | Clausen et al. |
| 7,867,286 B2 | 1/2011 | Einarsson |
| 7,868,511 B2 | 1/2011 | Calley |
| 7,879,110 B2 | 2/2011 | Phillips |
| 7,883,546 B2 * | 2/2011 | Kazerooni et al. ............ 623/27 |
| 7,891,258 B2 | 2/2011 | Clausen et al. |
| 7,892,195 B2 | 2/2011 | Grim et al. |
| D634,438 S | 3/2011 | Hu |
| D634,852 S | 3/2011 | Hu |
| 7,896,826 B2 | 3/2011 | Hu et al. |
| 7,896,827 B2 | 3/2011 | Ingimundarson et al. |
| 7,896,927 B2 | 3/2011 | Clausen et al. |
| 7,909,884 B2 | 3/2011 | Egilsson et al. |
| 7,910,793 B2 | 3/2011 | Sigurjonsson et al. |
| 7,914,475 B2 | 3/2011 | Wyatt et al. |
| 7,918,765 B2 | 4/2011 | Kruijsen et al. |
| D637,942 S | 5/2011 | Lee et al. |
| 7,935,068 B2 | 5/2011 | Einarsson |
| D640,380 S | 6/2011 | Tweardy et al. |
| D640,381 S | 6/2011 | Tweardy et al. |
| 7,955,398 B2 | 6/2011 | Bedard et al. |
| 7,959,589 B2 | 6/2011 | Sreeramagiri et al. |
| D641,482 S | 7/2011 | Robertson et al. |
| D641,483 S | 7/2011 | Robertson et al. |
| 7,981,068 B2 | 7/2011 | Thorgilsdottir et al. |
| 7,985,193 B2 | 7/2011 | Thorsteinsson et al. |
| 7,985,265 B2 | 7/2011 | Moser et al. |
| D643,537 S | 8/2011 | Lee |
| 7,998,221 B2 | 8/2011 | Lecomte et al. |
| 8,002,724 B2 | 8/2011 | Hu et al. |
| 8,007,544 B2 | 8/2011 | Jonsson et al. |
| 8,016,781 B2 | 9/2011 | Ingimundarson et al. |
| 8,021,317 B2 | 9/2011 | Arnold et al. |
| 8,025,632 B2 | 9/2011 | Einarsson |
| 8,025,699 B2 | 9/2011 | Lecomte et al. |
| 8,026,406 B2 | 9/2011 | Janusson et al. |
| D646,394 S | 10/2011 | Tweardy et al. |
| D647,622 S | 10/2011 | Lee et al. |
| D647,623 S | 10/2011 | Thorgilsdottir et al. |
| D647,624 S | 10/2011 | Thorgilsdottir et al. |
| 8,034,120 B2 | 10/2011 | Eglisson et al. |
| 8,038,636 B2 | 10/2011 | Thorgilsdottir et al. |
| 8,043,244 B2 | 10/2011 | Einarsson et al. |
| 8,043,245 B2 | 10/2011 | Campos et al. |
| 8,048,007 B2 | 11/2011 | Roy |
| 8,048,013 B2 | 11/2011 | Ingimundarson et al. |
| 8,048,172 B2 | 11/2011 | Jonsson et al. |
| 8,052,760 B2 | 11/2011 | Egilsson et al. |
| 8,057,550 B2 | 11/2011 | Clausen et al. |
| 8,065,105 B2 * | 11/2011 | Bar-Haim et al. ............ 702/97 |
| 8,202,325 B2 | 6/2012 | Albrecht-Laatsch et al. |
| 8,617,254 B2 * | 12/2013 | Bisbee et al. ................. 623/24 |
| 2001/0029400 A1 | 10/2001 | Deffenbaugh et al. |
| 2002/0052663 A1 | 5/2002 | Herr et al. |
| 2002/0092724 A1 | 7/2002 | Koleda |
| 2002/0138153 A1 | 9/2002 | Koniuk |
| 2003/0093021 A1 | 5/2003 | Goffer |
| 2003/0125814 A1 | 7/2003 | Paasivaara et al. |
| 2003/0139783 A1 | 7/2003 | Kilgore et al. |
| 2003/0163206 A1 | 8/2003 | Yasui et al. |
| 2003/0195439 A1 | 10/2003 | Caseinova |

(56) References Cited

U.S. PATENT DOCUMENTS

| | | | |
|---|---|---|---|
| 2004/0039454 | A1 | 2/2004 | Herr et al. |
| 2004/0049290 | A1 | 3/2004 | Bedard |
| 2004/0054423 | A1 | 3/2004 | Martin |
| 2004/0064195 | A1 | 4/2004 | Herr |
| 2004/0088025 | A1 | 5/2004 | Gesotti |
| 2004/0181118 | A1 | 9/2004 | Kochamba |
| 2005/0049652 | A1 | 3/2005 | Tong |
| 2005/0059908 | A1 | 3/2005 | Bogert |
| 2005/0070834 | A1* | 3/2005 | Herr .................... A61B 5/1038 602/28 |
| 2005/0085948 | A1 | 4/2005 | Herr et al. |
| 2005/0155444 | A1 | 7/2005 | Otaki et al. |
| 2005/0251079 | A1* | 11/2005 | Carvey et al. ................. 602/26 |
| 2006/0004307 | A1 | 1/2006 | Horst |
| 2006/0069448 | A1 | 3/2006 | Yasui |
| 2006/0094989 | A1 | 5/2006 | Scott et al. |
| 2006/0135883 | A1 | 6/2006 | Jonsson et al. |
| 2006/0173552 | A1* | 8/2006 | Roy ................................ 623/24 |
| 2006/0184280 | A1* | 8/2006 | Oddsson et al. .............. 700/245 |
| 2006/0224246 | A1 | 10/2006 | Clausen et al. |
| 2006/0249315 | A1 | 11/2006 | Herr et al. |
| 2006/0258967 | A1 | 11/2006 | Fujil et al. |
| 2006/0276728 | A1 | 12/2006 | Ashihara et al. |
| 2007/0016329 | A1 | 1/2007 | Herr et al. |
| 2007/0043449 | A1 | 2/2007 | Herr et al. |
| 2007/0123997 | A1 | 5/2007 | Herr et al. |
| 2007/0162152 | A1 | 7/2007 | Herr et al. |
| 2008/0039756 | A1* | 2/2008 | Thorsteinsson et al. ....... 602/23 |
| 2008/0114272 | A1 | 5/2008 | Herr et al. |
| 2008/0155444 | A1 | 6/2008 | Pannese et al. |
| 2009/0030530 | A1 | 1/2009 | Martin |
| 2009/0171469 | A1 | 7/2009 | Thorsteinsson et al. |
| 2009/0222105 | A1 | 9/2009 | Clausen |
| 2009/0265018 | A1* | 10/2009 | Goldfarb ................... A61F 2/60 623/40 |
| 2010/0025409 | A1 | 2/2010 | Hunter |
| 2010/0113980 | A1* | 5/2010 | Herr .......................... A61F 2/60 600/587 |
| 2010/0114329 | A1 | 5/2010 | Casler et al. |
| 2010/0179668 | A1 | 7/2010 | Herr et al. |
| 2010/0312363 | A1 | 12/2010 | Herr et al. |
| 2011/0224804 | A1 | 9/2011 | Clausen et al. |
| 2011/0245931 | A1 | 10/2011 | Clausen et al. |

FOREIGN PATENT DOCUMENTS

| | | |
|---|---|---|
| WO | WO-2004017872 | 3/2004 |
| WO | WO-2004019832 | 3/2004 |
| WO | WO-2006110895 | 10/2006 |
| WO | WO-2009082249 | 7/2009 |
| WO | WO-2010025409 | 3/2010 |
| WO | WO-2010027968 | 3/2010 |

OTHER PUBLICATIONS

Chen, I.H. The influence of walking speed on mechanical joint power during gait. Gait and Posture. 6 (1997) 171-176.*

Devita, Paul. Eccentric but not concentric muscle work is retained with age in level walking. American Society of Biomechanics 2007 Annual Conference. Aug. 22-25, 2007.*

U.S. Appl. No. 13/349,216, filed Jan. 12, 2012, Zhixiu Han.

U.S. Appl. No. 13/347,443, filed Jan. 10, 2012, Zhixiu Han.

U.S. Appl. No. 13/356,230, filed Jan. 23, 2012, Zhixiu Han.

U.S. Appl. No. 13/417,949, filed Mar. 12, 2012, Hugh M. Herr.

Abbas J. and Chizeck H., "Neural Network Control of Functional Neuromuscular Stimulation Systems: Computer Simulation Studies," IEEE Transactions on Biomedical Engineering, vol. 42, No. 1, Nov. 1995, pp. 1117-1127.

Abui-haj, C. and Hogan, N., "Functional assessment of control systems for cybernetic elbow prostheses. Part I, Part II," IEEE Transactions on Biomedical Engineering, vol. 37, No. 11, Nov. 1990, Cambridge, MA, pp. 1025-1047.

Akazawa, K., et. al, "Biomimetic EMG prosthesis-hand," Proceedings of the 18th Annual International Conference of the IEEE Engineering in Medicine and Biology Society, vol. 2, Oct. 1996, Amsterdam, Netherlands, pp. 535-536.

Aminian, "Estimation of Speed and Incline of Walking Using Neural Network," IEEE Transactions on Biomedical Engineering, vol. 44, No. 3, Jun. 1995, pp. 743-746.

Anderson, F. and Pandy M., "Dynamic optimization of human walking," Journal of Biomechanical Engineering, vol. 123, Oct. 2001, pp. 381-390.

Andrews, et al., "Hybrid FES Orthosis incorporating closed loop control and sensory feedback," J. Biomed Eng., vol. 10, Apr. 1988, pp. 189-195.

Arakawa, T. and Fukuda, T., "Natural motion generation of biped locomotion robot using hierarchical trajectory generation method consisting of GA, EP layers," Proceedings of the 1997 IEEE International Conference on Robotics and Automation, Apr. 1997, Albuquerque, NM, pp. 211-216.

Au., et. al., "Powered Ankle-Foot Prosthesis for the Improvement of Amputee Ambulation," Proceedings of the 29th Annual International Conference of the IEEE, Aug. 2007, Lyon, France, pp. 3020-3026.

Au, S., "An EMG-position controlled system for an active ankle-foot prosthesis: an initial experimental study," Proc. of the 2006 IEEE International Conference on Rehabilitation Robotics, Jul. 2005, Chicago, IL, pp. 375-379.

Au, S. and Herr H., "Initial experimental study on dynamic interaction between an amputee and a powered ankle-foot prosthesis," Workshop on Dynamic Walking: Mechanics and Control of Human and Robot Locomotion, May 2006, Ann Arbor, MI, p. 1.

Au, S., et al. "An ankle-foot emulation system for the study of human walking biomechanics," Proc. of the 2006 IEEE Int. Conf. on Robotics and Automation, May 2006, Orlando, FL, pp. 2939-2945.

Au, S., et. al., "Biomechanical design of a powered ankle-foot prosthesis," Proc. of the 2007 IEEE Int. Conf. on Rehabilitation Robotics, Jun. 2007, Noordwijk, Netherlands, pp. 298-303.

Au, S., et. al., "Powered ankle-foot prosthesis to assist level-ground and stair-descent gaits," Neural Networks, vol. 21, No. 4, Mar. 2008, pp. 654-666.

Au, S., et. al., "Powered Ankle-foot Prosthesis Improves Walking Metabolic Economy," IEEE Trans. on Robotics, vol. 25, No. 1, Feb. 2009, pp. 51-66.

Barth, D., et. al., "Gait analysis and energy cost of below-knee amputees wearing six different prosthetic feet," Journal of Prosthetics & Orthotics, vol. 4, No. 2, Winter, 1992, pp. 63-75.

Baten, et al., "Inertial Sensing in Ambulatory back load Estimation," 18 Annual International Conferences of IEEE Engineering in Medicine and Biology Society, Amsterdam 1996, pp. 497-498.

Bateni, H. and Olney S., "Kinematic and kinetic variations of below-knee amputee gait," Journal of Prosthetics & Orthotics, vol. 14, No. 1, Mar. 2002, pp. 2-13.

Blaya, J. and Herr, H, "Adaptive control of a variable-impedance ankle-foot orthosis to assist drop-foot gait," IEEE Transactions on Neural Systems and Rehabilitation Engineering, vol. 12, No. 1, Mar. 2004, pp. 24-31.

Blaya, J.A., and Herr, H., "Adaptive Control of a Variable-Impedance Ankle-Foot Orthosis to Assist Drop Foot Gait," Artificial Intelligence Lab and Harvard—MIT Division Health Sciences and Technology, Boston, MA, 30 pages.

Blaya, J.A., et al., "Active Ankle Foot Orthoses (AAFO)," http://www.ai.mit.edu. Artificial Intelligence Laboratory, Massachusetts Institute of Technology, Cambridge, Massachusetts, 3 pages.

Blaya, J.A., "Force-Controllable Ankle Foot Orthosis (AFO) to Assist Drop Foot Gait," submitted to the Department of Mechanical Engineering, Massachusetts Institute of Technology, Cambridge, Massachusetts (Feb. 2003), 88 pages.

Blickhan, R., "The spring-mass model for running and hopping," J of Biomech. Feb. 22, 1989, Great Britain, pp. 1217-1227.

Bortz, "A New Mathematical Formulation for Strapdown Inertial Navigation," IEEE Transactions of Aerospace and Electronic Systems, vol. AES-7, No. 1, Jan. 1971, p. 61-66.

(56) References Cited

OTHER PUBLICATIONS

Brockway, J., "Derivation of formulae used to calculate energy expenditure in man," Human Nutrition Clinical Nutrition, vol. 41, Nov. 1987, pp. 463-471.
Brown, R., "On the nature of the fundamental activity of the nervous centres: together with an analysis of the conditioning of rhythmic activity in progression, and a theory of the evolution of function in the nervous system," J Physiol, vol. 48, No. 1, Mar. 1914, pp. 18-46.
Chang, et al., Ischemic Colitis and Complications of Constipation Associated with the use of Alosetron Under a Risk Management Plan: Clinical Characteristics, Outcomes, and Incidences The Americal Journal of Gastronenterology, vol. 105, No. 4, Apr. 2010, pp. 866-875.
Chu, A., Kazerooni, H. and Zoss, A., "On the Biomimetic Design of the Berkeley Lower Extremity Exoskeleton (BLEEX)," Proceedings of the 2005 IEEE International Conference on Robotics and Automation, Apr. 2005, Barcelona, Spain, pp. 4356-4363.
Colborne, G. R., S. Naumann, P. E. Langmuir, and D. Berbrayer, "Analysis of mechanical and metabolic factors in the gait of congenital below knee amputees," Am. J. Phys. Med. Rehabil., vol. 92, pp. 272-278, Oct. 1992.
Collins, et al., "Controlled Energy Storage and Return Prosthesis Reduces Metabolic cost of Walking," ASB 29th Annual Meeting, Cleveland, Ohio, Jul. 31-Aug. 5, 2005, 1 page.
Collins, et al., "Supporting Online Material for Efficient bipedal robots based on passivedynamic walkers," Mechanical Engineering, University of Michigan, Feb. 2005, Ann Arbor, MI, pp. 1-8.
Crago P., et. al., "New Control Strategies for neuroprosthetic systems," Journal of Rehabilitation Research and Development, vol. 33, No. 2, Apr. 1996, pp. 158-172.
Daley, M.A., Felix, G., Biewener, A. A., 2007, Running stability is enhanced by a proximodistal gradient in joint neuromechanical control. J Exp Bioi 210 (Pt 3), Nov. 2006, pp. 383-394.
Dapena, J. and McDonald, C., "Three-dimensional analysis of angular momentum in the hammer throw," Med. Sci. in Sports Exerc., vol. 21, No. 2, Apr. 1989, pp. 206-220.
Dietz, V., "Proprioception and locomotor disorders," Nat Rev Neurosci, vol. 3, Oct. 2002, pp. 781-790.
Dietz, V., "Spinal Cord Pattern Generators for Locomotion," download Feb. 6, 2012, http://www.Clinoh-journal.com/article/PIIS1388245703001202/fulltext, 12 pages.
Doerschuk, et. al., "Upper extremity limb function discrimination using EMG signal analysis," IEEE Transactions on Biomedical Engineering. vol. 30., No. 1., Jan. 1983, pp. 18-28.
Doke, J., et. al., "Mechanios and energetics of swinging the human leg," The Journal of Experimental Biology, vol. 208, Feb. 2005, pp. 439-445.
Dollar, et al., "Lower Extremity Exoskeletons and Active Orthoses: Challenges and State-of-the-Art," IEEE Transactions on Robotics, vol. 24, No. 1, Feb. 2008, 15 pages.
Donelan, J., et. al., "Force regulation of ankle extensor muscle activity in freely walking cats," J Neurophysiol, vol. 101, No. 1, Nov. 2008, pp. 360-371.
Donelan, J., et. al., "Mechanical work for step-to-step transitions is a major determinant of the metabolic cost of human walking," J. Exp. Bioi., vol. 205, Dec. 2002, pp. 3717-3727.
Donelan, J., et. al. "Simultaneous positive and negative external mechanical work in human walking," Journal of Biomechanics, vol. 35, Jan. 2002, pp. 117-124.
Drake, C., "Ankle & Foot Splints or Orthoses," HemiHelp, Information Sheet 13 Last updated Jun. 2009, 5 pages.
Drake, C., "Ankle & Foot Splints or Orthoses (AFOs)," HemiHelp, Last updated Jun. 2009, 8 pages.
Drake, C., "Foot & Ankle Splints or Orthoses," HemiHelp Information Sheet, London, United Kingdom, 3 pages, www.hemihelp.org.uk/leaflets/hbleaflets90.htm.
Eilenberg, M., "A Neuromuscular-Model Based Control Strategy for Powered Ankle-Foot Prostheses," Master's Thesis, Massachusetts Institute of Technology, Cambridge, Mass., 2009.

Ekeberg, 0. and Grillner, S., "Simulations of neuromuscular control in lamprey swimming," Philos Trans R Soc Land B Bioi Sci, vol. 354, May 1999, pp. 895-902.
Ekeberg, 0. and Pearson, K., "Computer simulation of stepping in the hind legs of the cat: an examination of mechanisms regulating the stance-to-swing transition," J Neurophysiol, vol. 94, No. 6, Jul. 2005, pp. 4256-4268.
Endo, K., et. al., "A quasi-passive model of human leg function in level-ground walking," Proc. of 2006 IEEE/RSJ International Conference on Intelligent Robots and Systems (IROS), Oct. 2006, Beijing, China, pp. 4935-4939.
Eppinger, S. Seering W., "Three dynamic problems in robot force control," IEEE Transactions on Robotics and Automation, vol. 8, No. 6, Dec. 1992, pp. 751-758.
Esquenazi, A. and DiGiacomo, R., "Rehabilitation After Amputation," Journ Am Podiatr Med Assoc, vol. 91, No. 1, Jan. 2001, pp. 13-22.
Farley, C. and McMahon, T., "Energetics of walking and running: insights from simulated reduced-gravity experiments," The American Physiological Society, Dec. 1992, pp. 2709-2712.
Farry, K. A., et al., "Myoelectric teleoperation of a complex robotic hand," IEEE Transactions on Robotics and Automation. vol. 12, No. 5, Oct. 1996, pp. 775-788.
Featherstone, R., 1987, "Robot Dynamic Algorithms", Boston, Mass., Kluwer Academic Publishers, pp. 155-172.
Fite, K., et. al., "Design and Control of an Electrically Powered Knee Prosthesis," Proc. of 2007 IEEE 10th International Conference on Rehabilitation Robotics (ICORR), Jun. 2007, pp. 902-905.
Flowers, W. "A Man-interactive Simulator System for Above-Knee Prosthetic Studies," Ph.D. thesis, Massachusetts of Institute Technology, Department of Mechanical Engineering. Jul. 10, 1973.
Fod, A., et. al., "Automated Derivation of Primitives for Movements Classification," Autonomous Robots, vol. 12, No. 1, Jan. 2002, pp. 39-54.
Frigon, A. and Rossignol, S., "Experiments and models of sensorimotor interactions during locomotion," Bioi Cybern., vol. 95, No. 6, Nov. 2006, pp. 607-627.
Fujita K, et. al., "Joint angle control with command filter for human ankle movement using functional electrical stimulation," Proc. of IEEE Ninth Annual Conference for the Engineering in Medicine and Biology Society, Nov. 1987, Boston, MA, pp. 1719-1720.
Fukuda, 0. et al., "A human-assisting manipulator teleoperated by EMG signals and arm motions," IEEE Transactions on Robotics and Automation. vol. 19, No. 2, Apr. 2003, pp. 210-222.
Gates, D., "Characterizing ankle function during stair ascent, descent, and level walking for ankle prosthesis and orthosis design," Master's thesis, Boston University, 2004, pp. 1-82.
Gelritsen, K., et. al., "Direct dynamics simulation of the impact phase in heel-toe running," J. Biomech., vol. 28, No. 6, Jun. 1995, Great Britain, pp. 661-668.
Geyer, H., et. al., "Compliant leg behaviour explains the basic dynamics of walking and running," Proc. R. Soc. Cond. B 273, Aug. 2006, pp. 2861-2867.
Geyer, H., et. al., "Positive force feedback in bouncing gaits?," Proceedings of Royal Society B—Biological Sciences, vol. 270, No. 1529, Aug. 2003, pp. 2173-2183, 2003.
Geyer, H. and Herr H., "A muscle-reflex model that encodes principles of legged mechanics predicts human walking dynamics and muscle activities," IEEE Transactions on Neural Systems and Rehabilitations Engjneering, vol. 18, No. 3, Jun. 2010, pp. 263-273.
Ghigliazza, R., et. al., "A simply stabilized running model," SIAM J. Applied. Dynamical Systems, vol. 2, No. 2, May 2004, pp. 187-218.
Godha, el al., "Integrated GPS/INS System for Pedestrian Navigation in a Signal Degraded Environment," ION GNSS, Sep. 2006, Fort Worth, TX, pp. 1-14.
Goswami, A., "Postural stability of biped robots and the foot-rotation indicator (FRI) point," International Journal of Robotics Research, vol. 18, No. 6, Jun. 1999, pp. 523-533.
Goswami, A. and Kallem, V., "Rate of change of angular momentum and balance maintenance of biped robots," Proceedings of the 2004 IEEE International Conference on Robotics and Automation, Apr. 2004, New Orleans, La., pp. 3785-3790.

(56) References Cited

OTHER PUBLICATIONS

Graupe, D., et al., "A microprocessor system for multifunctional control of upper-limb prostheses via myoelectric signal identification," IEEE Transaction on Automatic Control. vol. AC-23, vol. 4, Aug. 1978, pp. 538-544.

Gregoire, L., and et al, "Role of mono- and bi-articular muscles in explosive movements," International Journal of Sports Medicine 5, 614-630. Dec. 1984.

Grillner, S. and Zangger, P., "On the central generation of locomotion in the low spinal cat," Exp Brain Res, vol. 34, No. 2, Jan. 1979, pp. 241-261.

Grimes, D. L., "An active multi-mode above-knee prosthesis controller," Ph.D. Thesis, Massachusetts Institute of Technology, Jul. 20, 1979.

Gu, W., "The Regulation of Angular Momentum During Human Walking," Undergraduate Thesis, Massachusetts Institute of Technology, Physics Department, Jun. 2003, pp. 2-46.

Gunther, M., et. al., "Human leg design: optimal axial alignment under constraints," J. Math. Bioi., vol. 48, Mar. 2004, pp. 623-646.

Gunther, M. and Ruder, H., "Synthesis of two-dimensional human walking: a test of the Amodel," Bioi. Cybern., vol. 89, May 2003, pp. 89-106.

Hanalusa et al., "A Robot Hand with Elastic Fingers and Its Application to Assembly Process," pp. 337-359, Robot Motion, Brady et al., MIT Press, Cambridge, MA, 1982.

Hansen, A. H., Childress, D. S., Miff, S.C., Gard, S. A,, Mesplay, K. P., "The human ankle during walking: implication for the design of biomimetic ankle prosthesis," Journal of Biomechanics, vol. 37, No. 10, Oct. 2004, pp. 1467-1474.

Hayes et al., "Leg Motion Analysis During Gait by Multiaxial Accelerometry: Theoretical Foundations and Preliminary Validations," Journal of Biomechanical Engineering, vol. 105, Aug. 1983, pp. 283-289.

Heglund, N., "A Simple Design for a Force-Plat to Measure Ground Reaction Forces," J. Exp. Bioi., vol. 93, Aug. 1981, pp. 333-338.

Herr, H. and McMahon, T.,"A trolting horse model," Int. J. Robotics Res., vol. 19, No. 6, Jun. 2000, pp. 566-581.

Herr, H. and Popovic, M., "Angular momentum regulation in human walking," J. Exp. Bioi., vol. 211, Feb. 2008, pp. 467-481.

Herr, H. and Wilkenfeld A., "User-adaptive control of a magnetorheologioalprosthetic knee," Industrial Robot: An International Journal, vol. 30, No. 1, 2003, pp. 42-55.

Herr, H., et. al, "A model of scale effects in mammalian quadrupedal running," J Exp Bioi 205 (Pt 7), Apr. 2002, pp. 959-967.

Heyn et al., "The Kinematice of the Swing Phase Obtained from Accelerometer and Gyroscope Measurements," 18th Annual International Conference of the IEEE Engineering in Medicine and Biology Society, Nov. 1996, Amsterdam, Netherlands, pp. 463-464.

Hill, V., "The heat of shortening and the dynamic constants of muscle," Proceedings of the Royal Society London B, vol. 126, No. 843, Oct. 1938, pp. 136-195.

Hirai, K., et al., "The development of Honda humanoid robot," Proceedings on IEEE/RSJ International Conference on Intelligent Robots and Systems, May 1998, Leuven, Belgium, pp. 1321-1326.

Hitt, J., R. Bellman, M. Holgate, T. Sugar, and K. Hollander, "The sparky (spring ankle with regenerative kinetics) projects: Design and analysis of a robotic transtibial prosthesis with regenerative kinetics," In Proc. IEEE Int. Conf. Robot. Autom., Orlando, Fla., pp. 2939-2945, Sep. 2007.

Hof. A., et. al., "Calf muscle moment, work and efficiency in level walking; role of series elasticity," Journal of Biomechanics, vol. 16, No. 7, Sep. 1983, pp. 523-537.

Hofbaur, M. and Williams, B., "Hybrid Diagnosis with Unknown Behavioral Modes", Proceedings of the 13.sup.th International Workshop on Principles of Diagnosis (DX02), May 2002, pp. 1-10.

Hofbaur, M. and Williams, B., "Mode Estimation of Probabitistic Hybrid Systems", HSSC 2002, LNCS 2289, Mar. 25, 2002, pp. 253-266.

Hofmann, A., et. al., "A Sliding Controller for Bipedal Balancing Using Integrated Movement of Contact and Non-Contact Limbs," Proceedings of the IEEE/RSJ International Conference on Intelligent Robots and Systems, Sep. 2004, Sendai, Japan, pp. 1952-1959.

Hofmann, A., et. al., "Robust Execution of Bipedal Walking Tasks from Biomechanical Principles," Doctor of Philosophy at the Massachusetts Institute of Technology, Jan. 2006, 407 pages.

Hogan, N and Buerger S., "Impedance and Interaction Control," Robotics and Automation Handbook, CRC Press, Jun. 2004, pp. 19.1-19.24.

Hogan, N. (1976) A review of the methods of processing EMG for use as a proportional control signal. Biomedical Engineering. pp. 81-86.

Hogan, N., "Impedance Control: An Approach to Manipulation: Part I—Theory," Journal of Dynamic Systems, Measurement, and Control, vol. 107, Mar. 1985, pp. 1-7.

Hogan, N., "Impedance Control: An Approach to Manipulation: Part II—Implementation," Journal of Dynamic Systems, Measurement , and Control, 107:8-16, (1985).

Hogan, N., "Impedance Control: An Approach to Manipulation: Part III—Application," Journal of Dynamics Systems, Measurement, and Control, 107:17-24, (1985).

Hogan, N., "Impedance Control: An Approach to Manipulation," Dept. of Mechanical Engineering and Laboratory of Manufacturing and Productivity, Massachusetts institute of Technology, Cambridge MA, pp. 304-313, (Jun. 1984).

Hollander, K. W., T. G. Sugar, and D. E. Herring, "Adjustable robotic tendon using a 'Jack Spring' .TM.," Proceedings on IEEE International Conference on Rehabilitation Robotics, Chicago, pp. 113-118, Jun. 28, 2005.

Howard, "Joint and Actuator Design for Enhanced Stability in Robotic Force Control," Ph.D. thesis, Massachusetts Inst. of Technology, Dept. of Aeronautics and Astronautics, Sep. 19, 1990.

Huang, H. and Chen. C., "Development of a myoelectric discrimination system for a multi-degree prosthetic hand," Proceeding of the 1999 IEEE International Conference on Robotics and Automation, May 1999, Detroit, MI, pp. 2392-2397.

Huang, Q., "Planning walking patterns for a biped robot," IEEE Transactions on Robotics and Automation, vol. 17, No. 3, Jun. 2001, pp. 280-289.

Hultborn, H., Spinal reflexes, mechanisms and concepts: from Eccles to Lundberg and beyond, Prog Neurobioi, vol. 78, Feb. 2006, pp. 215-232.

Ijspeert, A. J., 2008, "Central pattern generators for locomotion control in animals and robots: a review," Neural Netw, vol. 21, No. 4, May 2008, pp. 642-653.

Ijspeert, A., et. al., "From swimming to walking with a salamander robot driven by a spinal cord model," Science, vol. 315, No. 5817, Mar. 2007, pp. 1416-1420.

International Search Report and Written Opinion for PCT/US2009/055600 dated Apr. 29, 2010 (23 pages).

International Search Report and Written Opinion for PCT/US2010/047279 dated Jan. 19, 2011 (11 pages).

International Search Report and Written Opinion for PCT/US2011/031105 dated Oct. 11, 2011 (16 pages).

International Search Report for PCT/US2012/020775 dated Jun. 1, 2012 (6 pages).

International Search Report for PCT/US2012/021084 dated Aug. 1, 2012 (3 pages).

International Search Report for PCT/US2012/022217 dated May 31, 2012 (6 pages).

Ivashko, D., et. al, "Modeling the spinal cord neural circuitry controlling cat hindlimb movement during locomotion," Neurocomputing, vol. 52-54, Mar. 2003, pp. 621-629.

Johansson, J., et al., "A clinical comparison of variable damping and mechanically passive prosthetic knee devices," American Journal of Physical Medicine & Rehabilitation, vol. 84, No. 8, Aug. 2005, pp. 563-575.

Johnson, C. and Lorenz R., "Experimental identification of friction and its compensation in precise, position controlled mechanisms," IEEE Trans. on Industry Applications, vol. 28, No. 6, Dec. 1992, pp. 1392-1398.

Jonic S, et. al., "Three machine learning techniques for automatic determination of rules to control locomotion," IEEE Trans Biomed Eng, vol. 46, No. 3, Mar. 1999, pp. 300-310.

(56) References Cited

OTHER PUBLICATIONS

Kadaba, M., et. al., "Measurement of lower extremity kinernatics during level walking," J. Orthop. Res., vol. 8, May 1990, pp. 383-392.

Kadaba, M., et. al., "Repeatability of kinematic, kinetic, and electromyographic data in normal adult gait," J. Orthop. Res., vol. 7, Nov. 1989, pp. 849-860.

Kajita, K., et. al., "Biped walking on a low friction floor," Proceedings of the 2004 IEEE/RSJ International Conference on Intelligent Robots and Systems, Oct. 2004, Sendai, Japan., pp. 3546-3551.

Kajita, S., et. al., "A Hop towards Running Humanoid Biped," Proceedings of the 2004 IEEE Internationl Conference on Robotics and Automation, Apr. 2004, New Orleans, La., pp. 629-635.

Kajita, S., et. al., "Resolved Momentum Control: Humanoid Motion Planning based on the Linear and Angular Momentum," Proceedings of the 2003 IEEE/RSJ International Conference on Intelligent Robots and Systems, Oct. 2003, Las Vegas, Nev., pp. 1644-1650.

Kaneko, K., et al., "Humanoid robot HRP-2," Proc. IEEE Int. Conf. on Robotics and Automation, Apr. 2004, New Orleans, La., pp. 1083-1090.

Kapti, A. and Yucenur M., "Design and control of an active artificial knee joint," Mechanism and Machine Theory, vol. 41, Apr. 2006, pp. 1477-1485.

Katie, D. and Vukobratovic, M., "Survey of intelligent control techniques for humanoid robots," Journal of Intelligent and Robotics Systems, vol. 37, Jun. 2003, pp. 117-141.

Kerrigan, D, et. al., "A refined view of the determinants of gait: significance of heel rise," Arch. Phys. Med. Rehab., vol. 81, Aug. 2000, pp. 1077-1080.

Kerrigan, D, et. al., "Quantification of pelvic rotation as a determinant of gait," Arch. Phys. Med. Rehab., vol. 82, Feb. 2001, pp. 217-220.

Khatib, O., et. al., "Coordination and decentralized cooperation of multiple mobile manipulators," Journal of Robotic Systems, vol. 13, No. 11, Nov. 1996, pp. 755-764.

Khatib, O., et. al., "Whole body dynamic behavior and control of human-like robots," International Journal of Humanoid Robotics, vol. 1, No. 1, Mar. 2004, pp. 29-43.

Kidder, et al., "A System for the Analysis of Fool and Ankle Kinematics During Gait," IEEE Transactions on Rehabilitation Engineering, vol. 4, No. 1, Mar. 1996, pp. 25-32.

Kim, et al., "Realization of Dynamic Walking for the Humaniod Robot Platform KHR-1," Advanced Robotics, vol. 18, No. 7, pp. 749-768, (2004).

Kirkwood C, et. al., "Automatic detection of gait events: a case study using inductive learning techniques.," J Biomed Eng, vol. 11, Nov. 1989, pp. 511-516.

Kitayama, I., Nakagawa N, Amemori K, "A microcomputer controlled Intelligent A/K prosthesis," Proceedings of the 7th World Congress of the International Society for Prosthetics and Orthotics, Chicago. Jun. 28, 1992.

Klute, et al., Artificial Muscles: Actuators for Lower Limb Prostheses, Abstract in: Proceedings of the 2nd Annual Meeting of the VA rehabilitation Research and Development Service, Feb. 20-22, 2000, p. 107.

Klute, et al., "Artificial Muscles: Actuators for Biorobotic Systems," The International Journal of Robotics Research, vol. 21, No. 4, Apr. 2002, pp. 295-309.

Klute, et al., "Artificial Tendons: Biomechanical Design Properties for Prosthetic Lower Limbs," Chicago 2000 World Congress on Medical Physics and Biomedical Engineering, Chicago on Jul. 24-28, 2000, 4 pages.

Klute, et al., Intelligent Transtibial Prostheses with Muscle-Like Actuators,: 2002 American Physiological Society Intersociety Meeting: The Power of Comparative Physiology: Evolution, Integration, and Applied, 1 page.

Klute, et al., "Lower Limb Prostheses Powered by Muscle-Like Pneumatic Actuator," Submitted to Oleodinarnica o Pneumatica, Publishe Tecniche Nuove, Milamo, Italy, Mar. 15, 2000, 6 pages.

Klute, et al., "McKibben Artificial Muscles: Pneumatic Actuators with Biomechanical Intelligence," IEEE/ASME 1999 International Conference on Advanced Intelligent Mechatronics, Atlanta, GA, Sep. 19-22, 1999, pp. 221-226.

Klute, el al., "Muscle-Like Pneumatic Actuators for Below-Knee Prostheses," Actuator2000:7th International Conference on New Actuators, Bremen, Germany on Jun. 9-21, 2000, pp. 289-292.

Klute et al., "Powering Lower Limb Prosthestics with Muscle-Like Actuators," Abstract in: Proceeding of the 1st Annual Meeting of the VA Rehabilitation Research and Development Service, "Enabling Veterans: Meeting the Challenge of Rehabilitation in the Next Millennium," Washington, D.C., Oct. 1-3, 1998, p. 52.

Klute, et al., "Variable Stiffness Prosthesis for Transtibial Amputees," Dept of Veteran Affairs, Seattle, WA USA, 2 pages.

Klute, G., et. al., "Mechanical properties of prosthetic limbs adapting to the patient," Journal of Rehabilitation Research and Development, vol. 38, No. 3, May 2001, pp. 299-307.

Koganezawa, K. and Kato, t., "Control aspects of artificial leg," IFAC Control Aspects of Biomedical Engineering, 1987, pp. 71-85.

Kondak, K. and Hommel, G., "Control and online computation of stable movement for biped robots," Proc. of the 2003 IEEE/RSJ International Conference on Intelligent Robots and Systems (IROS), Oct. 2003, Las Vegas, Nev., pp. 874-879.

Kostov A., et. al., "Machine learning in control of functional electrical stimulation (FES) systems for locomotion," IEEE Trans an Biomed Eng, vol. 42, No. 6, Jun. 1995, pp. 541-551.

Kuo, A., "A simple model of bipedal walking predicts the preferred speed—step length relationship," Journal of Biomechanical Engineering, vol. 123, Jun. 2001, pp. 264-269.

Kuo, A., "Energetics of actively powered locomotion using the simplest walking model," Journal of Biomechanical Engineering, vol. 124, Feb. 2002, pp. 113-120.

LaFortune, "Three-Dimensional Acceleration of the Tibia During Walking and Running," J. Biomechanics, vol. 24, No. 10, 1991, pp. 877-886.

LeBlanc, M. and Dapena, J., "Generation and transfer of angular momentum in the javelin throw," Presented at the 20th annual meeting of the American Society of Biomechanics, Oct. 1996, Atlanta, Ga., pp. 17-19.

Li, C., et al. (Jun. 25, 2006) Research and development of the intelligently-controlled prosthetic ankle joint. Proc. of IEEE Int. Conf. on Mechatronics and Automation. Luoyang, China, pp. 1114-1119.

Liu, X., Low, K. H., Yu, H. Y., Sep. 2004 'Development of a Lower Extremity Exoskeleton for Human performance Enhancement', IEEE Conf. on Intelligent Robots and Systems, Sendai, Japan.

Light, et. al., Skeletal Transients on Heel Strike in Normal Walking With Different Footwear. J. Biomechanics vol. 13, pp. 477-480.

Lloyd R. and Cooke C., "Kinetic changes associated with load carriage using two rucksack designs," Ergonomics, vol. 43, No. 9, Sep. 2000, pp. 1331-1341.

Luinge, "Inertial Sensing of Human Movement," Twente University Press, ISBN 9036518237, 2002, pp. 1-80.

Lundberg, A., Oct. 19, 1968. Reflex control of stepping. In: The Nansen memorial lecture V. Oslo: Universitetsforlaget, 5-42.

Macfarlane, P., "Gait comparisons for below-knee amputees using a flex-foot versus a conventional prosthetic foot," Journal of Prosthetics & Orthotics, vol. 3, No. 4, Summer, 1991, pp. 150-161.

Maganaris, C., "Force-length characteristics of in vivo human skeletal muscle," Acta Physiol. Scand., vol. 172, Aug. 2001, pp. 279-285.

Maganaris, C., "Force-length characteristics of the in vivo human gastrocnemius muscle," Clin. Anal., vol. 16, May 2003, pp. 215-223.

Martens, W.L.J., "Exploring the Information Content and Some Applications of Body Mounted Plezo-Resistive Accelerometers," In: P.H. Voltink and R.C. van Lummel (eds.), Dynamic Analysis using Body Fixed Sensors, ISBN 90-9007328-0, 1994, pp. 8-11.

Maufroy, C., Towards a general neural controller for quadrupedal locomotion, Neural Netw, vol. 21, No. 4, Apr. 2008, pp. 667-681.

(56) References Cited

OTHER PUBLICATIONS

Mayagoitia R., et al., "Accelerometer and rate gyroscope measurement of kinematics: an inexpensive alternative to optical motion analysis systems," Journal of Biomechanics, vol. 35, Apr. 2002, pp. 537-542.
McFadyen, B. and Winter, D., "An integrated biomechanical analysis of normal stair ascent and descent," Journal of Blomechanics, vol. 21, No. 9, 1988, Great Britain, pp. 733-744.
McGeer T., "Passive Dynamic Walking," International Journal of Robotics, vol. 9, No. 2, May 1988, pp. 62-82.
McGeer, T., "Principles of walking and running," Advances in Comparative and Environmental Physiology, vol. 11, Ch. 4, Apr. 1992, pp. 113-139.
Mcintosh, A., et. al., "Gait dynamics on an inclined walkway," Journal of Biomechanics, vol. 39, Sep. 2005, pp. 2491-2502.
McMahon, T., "The mechanics of running: how does stiffness couple with speed?," J. of Biomecb., vol. 23, 1990, pp. 65-78.
McMahon, T., et. al., "Groucho Running," Journal of Applied Physiology, vol. 62, No. 6, Jun. 1987, pp. 2326-2337.
Minassian, K., et. al., "Human lumbar cord circuitries can be activated by extrinsic tonic input to generate locomotor-like activity," Hum. Mov. Sci., vol. 26, Mar. 2007, pp. 275-295.
Mochon, S., el. al., "Ballistic walking," Journal of Biomechanics, vol. 13, Dec. 1980, pp. 49-57.
Molen, N., "Energy/speed relation al below-knee amputees walking on motor-driven treadmill," Int. Z. Angew. Physio, vol. 31, Mar. 1973, pp. 173.
Morris, "Accelerometry—A Technique for the Measurement of Human Body Movements," J. Biomechanics, vol. 6, Nov. 1973, pp. 729-736.
Muraoka, T., et. al, "Muscle fiber and tendon length changes in the human vastus lateralis during slow pedaling," J. Appl. Physiol., vol. 91, Nov. 2001, pp. 2035-2040.
Nakagawa A., "Intelligent Knee Mechanism and the Possibility to Apply the Principle to the Other Joints," Proceedings of the 20th Annual International Conference of the IEEE Engineering in Medicine and Biology Society, Vo. 20, No. 5, Oct. 1998, pp. 2282-2287.
Neal R. and Hinton G., "A view of the EM algorithm that justifies incremental, sparse, and other variants," In Michael I. Jordan (editor), Learning in Graphical Models, 1999, Cambridge, MA, pp. 1-14.
Ng, et al.. "Fuzzy Model Identification for Classification of Gait Events in Paraplegics," IEEE Transactions on Fuzzy Systems, vol. 5, No. 4, Nov. 1997, pp. 536-544.
Nielsen, D., et. al., "Comparison of energy cost and gait efficiency during ambulation in below-knee amputees using different prosthetic feet—a preliminary report," Journal of Prosthetics & Orthotics, vol. 1, No. 1, 1989, pp. 24-29.
Oda, T, Ketal., 2005, "In vivo length-force relationships on muscle fiver and muscle tendon complex in the tibialis anterior muscle." Int. J. Sport and Health Sciences 3, 245-252.
Ogihara, N. and Yamazaki, N., "Generation of human bipedal locomotion by a bio-mimetic neuro-musculo-skeletal model," Bioi Cybern, vol. 84, No. 1, Jan. 2001, pp. 1-11.
Palmer, M., "Sagittal plane characterization of normal human ankle function across a range of walking gait speeds," Master's Thesis, MIT, Feb. 2002, Cambridge, MA, pp. 1-71.
Paluska, D., and Herr, H., "Series Elasticity and Actuator Power Ouput," Proceedings of the 2006 IEEE International Conference or Robotics and Automation, May 2005, Orlando, FL, pp. 1830-1833.
Paluska, D., and Herr, H., "The effect of series elasticity on actuator power and work output: implications for robotic and prosthetic joint design," Robotics and Autonomous Systems, vol. 54, Jun. 2006, pp. 667-673.
Pang, M., et. al., "The initiation of the swing phase in human infant stepping: importance of hip position and leg loading," J Physiol, vol. 528, No. 2, Oct. 2000, pp. 389-404.
Pasch, K. A., and W. P. Sewing, "On the drive systems for high performance machines," AMSE J. Mechanisms, Transmissions, and Automation in Design vol. 106, pp. 102-108, Mar. 1984.

Paul, C., et. al., "Development of a human neuro-musculo-skeletal model for investigation of spinal cord injury," Bioi Cybern, vol. 93, No. 3, Aug. 2005, pp. 153-170.
Pearson, K., "Generating the walking gait: role of sensory feedback," Prog Brain Res, vol. 143, 2004, pp. 123-129.
Pearson, K., et. al., "Assessing sensory function in locomotor systems using neuro-mechanical simulations," Trends Neurosci, vol. 29, No. 11, Nov. 2006, pp. 625-631.
Perry, Gait Analysis: Normal and Pathological Function, New Jersey: SLACK Inc.; 1992, Book Review, 1 page.
Perry, J. and S. Shanfield, "Efficiency of dynamic elastic response prosthetic feet," Journal of Rehabilitation Research and Development, vol. 30, No. 1, 1993 pp. 137-143.
Petrofshy et al., "Feedback Control Systernfor Walking In Man," Comput. Bioi. Med., vol. 14, No. 2, Mar. 1984, pp. 135-149.
Pfeffer et al., "Experiments with a Dual-Armed, Cooperative, Flexible-Drivetrain Robot System," Proc. 1993 IEEE Int. Conf. on Robotics & Automation, vol. 3, pp. 601-608, May 5, 1993.
Papovic, et al., "Gait Identification and Recognition Sensor," Proceedings of 6th Vienna International Workshop on Functional Electrostimulation, Sep. 1998, pp. 1-4.
Popovic, D., "Control of Movement for the Physically Disabled," Springer-Verlag London Limited, May 2000, pp. 270-302.
Popovic D., et al., "Control Aspects of Active Above-Knee Prosthesis," Int. Journal Man-Machine Studies, (1991) 35, pp. 751-767.
Popovic, M., "Angular Momentum Primitives for Human Walking: Biomechanics and Control," Proc. of the 2004 IEEE/RSJ International Conference on Intelligent Robots and Systems, Sep. 2004, Sendai, Japan., pp. 1685-1691.
Popovic, M., et. al., "Angular Momentum Regulation during human walking: Biomechanics and Control," Proceedings of the 2004 IEEE International Conference on Robotics and Automation, Apr. 2004, New Orleans, LA, pp. 2405-2411.
Popovic, M., et. al., "Zero spin angular momentum control: definition and applicability," Proceedings of the IEEE-RAS/RSJ International Conference on Humanoid Robots, Nov. 2004, Los Angeles, CA, pp. 1-16.
Popovic, M., et. al., "Ground Reference Points in Legged Locomotion: Definitions, Biological Trajectories and Control Implications," International Journal of Robotics Research, Dec. 2006, pp. 79-104.
Popovic, M. and Herr, H., "Global Motion Control and Support Base Planning," Proceedings of the IEEE/RSJ International Conference on Intelligent Robots and Systems, Aug. 2005, Alberta, Canada, pp. 1-8.
Popovic, M.B., W. Gu and H. Herr, "Conservation of Angular Momentum in Human Movement," MIT AI Laboratory-Research Abstracts, Sep. 2002. pp. 231-232, 2002.
Pratt, G. and Williamson M., "Series elastic actuators," Proceedings on IEEE/RSJ International Conference on Intelligent Robots and Systems, Jan. 1995, Pittsburgh, PA, pp. 399-406.
Pratt, G., "Legged Robots: What's New Since Raibert," IEEE Robotics and Automation Magazine, Research Perspectives, Sep. 2000, pp. 15-19.
Pratt G., "Low Impedance Walking Robots," Integ. and Camp. Bioi., vol. 42, Feb. 2002, pp. 174-181.
Pratt, J., et. al., "The RoboKnee: An Exoskeleton for Enhancing Strength and Endurance During Walking" IEEE Conf. on Robotics and Automation, Apr. 2004, Now Orleans, LA, pp. 2430-2435.
Prochazka, A. and Yakovenko, S., "The neuromechanical tuning hypothesis," Prog Brain Res, vol. 165, Oct. 2007, pp. 255-265.
Prochazka, A., et. al., "Positive force feedback control of muscles," J. of Neuro-phys., vol. 77, Jun. 1997, pp. 3226-3236.
Prochazka, A., et. al., "Sensory control of loomotion: reflexes versus higher-level control," Adv Exp Med Bioi, vol. 508, 2002, pp. 357-367.
Raibert, M., "Legged Robots that Balance," The MIT Press, Nov. 1986, Cambridge, MA, p. 89.
Rassier, D., et. al., "Length dependence of active force production in skeletal muscle," Journal of Applied Physiology, vol. 86, Issue 5, May 1999, pp. 1455-1457.
Riener, R., et. al., "Stair ascent and descent at different inclinations," Gait Posture, vol. 15, Feb. 2002, pp. 32-44.

(56) References Cited

OTHER PUBLICATIONS

Reitman, et. al., Gait analysis in prosthetics: opinions, Ideas and conclusions, Prosthetics and Orthotics international, 2002, 26, 50-57.
Robinson, D., "Design and an analysis of series elasticity in closed-loop actuator force control," Ph.D. Thesis, MIT, Jun. 2000, Cambridge, MA, pp. 1-123.
Robinson, D., "Series elastic actuator development for a biomimetic walking robot," Proceedings of IEEE/ASME International Conference on Advanced Intelligent Mechatronics, Sep. 1999, pp. 561-568.
Rosen, J., et al., "A myosignal-based powered exoskeleton system," IEEE Transactions on Systems, Man, and Cybernetics—Part A: Systems and Humans, vol. 31, No. 3, May 2001, pp. 210-222.
Ruina, A., et. al., "A collisional model of the energetic cost of support work qualitatively explains leg sequencing in walking and galloping, pseudo-elastic leg behavior in running and the walk-to-run transition," Journal of Theoretical Biology, vol. 237, Issue 2, Jun. 2005, pp. 170-192.
Rybak, I., et. al., "Modelling spinal circuitry involved in locomotor pattern generation: insights from deletions during fictive locomotion," J Physiol, vol. 577 (Pt 2), Dec. 2001, 617-639.
Sanderson, D., et. al., "Lower extremity kinematic and kinetic adaptations in unilateral below-knee amputees during walking," Gait and Posture, vol. 6, No. 2, Oct. 1997, pp. 126-136.
Sanger, T., "Human arm movements described by a low-dimensional superposition of principal component," Journal of NeuroScience, vol. 20, No. 3, Feb. 2000, pp. 1066-1072.
Saranli, U., "RHex: A simple and highly mobile hexapod robot," Int. Jour. Rob. Res., vol. 20, No. 7, Jul. 2001, pp. 616-631.
Sarrigeorgidis K. and Kyriakopoulos K., "Motion control of the N.T.U.A. robotic snamek on a planar surface," Proc. of the 1998 IEEE International Conference on Robotics and Automation, May 1998, pp. 2977-2982.
Schaal, S., "Is imitation learning the route to humanoid robots?" Trends in Cognitive Sciences, vol. 3, Jun. 1999, pp. 233-242.
Schaal, S. and Atkeson, C., "Constructive incremental learning from only focal information," Neural Computation, vol. 10, No. 8, Nov. 1998, pp. 2047-2084.
Scott, S. and Winter, D., "Biomechanical model of the human foot: kinematics and kinetics during the stance phase of walking." J. Biomech., vol. 26, No. 9, Sep. 1993, 1091-1104.
Sentis, L. and 0. Khatib, "Task-Oriented Control of Humanoid Robots Through Prioritization," IEEE—RAS/RSJ International Conference on Humanoid Robots, Nov. 2004, Santa Monica, CA, pp. 1-16.
Seyfarth, A., "Swing-leg retraction: a simple control model for stable running," J. Exp. Biol., vol. 206, Aug. 2003, pp. 2547-2555.
Seyfarth, A., et. al., "A movement criterion for running," J. of Biomech., vol. 35, May 2002, pp. 649-655.
Seyfarth, A., et. al., "Stable operation of an elastic three-segmented leg," Biol.Cybern., vol. 84, 2001, pp. 365-382.
Simon F., et. al, "Convergent force fields organized in the frog's spinal cord," Journal of NeuroScience, vol. 13, No. 2, Feb. 1993, pp. 467-491.
Sinkjaer, T., et. al., "Major role for sensory feedback in soleus EMG activity in the stance phase of walking in man," J Physiol, vol. 523, No. 3, Mar. 2000, pp. 817-827.
Skinner, H. and Effeney D., "Gait analysis in amputees," Am J Phys Med, vol. 64, Apr. 1985, pp. 82-89.
Smidt et al., "An Automated Accelerometry System for Gait Analysis," J. Biomechanics, vol. 10, 1977, pp. 367-375.
Srinivasan, M., "Energetics of legged locomotion: Why is total metabolic cost proportional to the cost of stance work," Proc. on ISB XXth Congress and the American Society of Biomechanics Annual Meeting, Jul. 2003, Cleveland, OH, pp. 829.
Stepien, J., et al., "Activity Levels Among Lower-Limb Amputees: Self-Report Versus Step Activity Monitor," Arch. Phys. Med. Rehabil., vol. 88, No. 7, Jul. 2007, pp. 896-900.

Sugano et al., "Force Control of the Roboto Finger Joint equipped with Mechanical Compliance Adjuster," Proc. of the 1992 IEEE/RSJ Int. Conf. on Intel I. Robots & Sys., Jul. 1992, pp. 2005-2013.
Sugihara, T., et. al., "Realtime Humanoid Motion Generation through ZMP Manipulation based on Inverted Pendulum Control," Proceedings of the 2002 IEEE International Conference on Robotics and Automation, May 2002, Washington, DC, pp. 1404-1409.
Sup, F., "Design and Control of a Powered Transfemoral Prosthesis," The International Journal of Robotics Research, vol. 27, No. 2, Feb. 2008, pp. 263-273.
Taga, G., "A model of the neuro-musculo-skeletal system for human locomotion," Biol. Cybern., vol. 73, No. 2, Jul. 1995, pp. 97-111.
Takayuki "Biped Locomotion using Multiple Link Virtual Inverted Pendulum Model," Publication of Electronics Information and Systems Society, vol. 120, No. 2, Feb. 2000, 8 pages.
Thorough man, K. and R. Shadmehr, "Learning of action through adaptive combination of motor primitives," Nature, vol. 407, Oct. 2000, pp. 742-747.
Tomovic R. et al., "A Finite State Approach to the Synthesis of Bioengineering Control Systems," IEEE Transactions on Human Factors in Electronics, vol. 7, No. 2, Jun. 1966, pp. 65-69.
Tong, et al., "A Practical Gait Analysis System Using Gyroscopes," Medical Engineering & Physics, vol. 21, Mar. 1999, pp. 87-94.
Turker, K., "Electromyography: some methodological problems and issues," Physical Therapy, vol. 73, No. 10, Oct. 1993, pp. 698-710.
van den Bogert, A., "Exotendons for assistance of human locomotion," Biomedical Engineering Online, Oct. 2003, pp. 1-8.
van den Bogert, et al. "A Method for Inverse Dynamic Analysis Using Accelerometry," Journal Biomechanics, vol. 29, No. 7, 1996, pp. 949-954.
Veltink P., et al., "The Feasibility of Posture and Movement Detection by Accelerometry," D-7803-I377-1/93, IEEE, Oct. 1993, pp. 1230-1231.
Vukobratovic M. and Juridic, D., "Contributions to the synthesis of biped gait," IEEE Transactions on Biomedical Engineering, vol. BME-16, No. 1, Jan. 1969, pp. 1-6.
Vukobratovic M. and Stepanenko J., "Mathematical models of general anthropomorphic systems," Mathematical Biosciences, vol. 17, Aug. 1973, pp. 191-242.
Walsh, C., "Biomimetic Design of an Under-Actuated Leg Exoskeleton for Load-Carrying Augmentation," Master's Thesis MIT, Feb. 2006, pp. 1-94.
Waters, RL., "Energy cost of walking amputees: the influence of level of amputation," J Bone Joint Surg., vol. 58, No. 1, Jan. 1976, pp. 42-46.
Wilkenfeld, A., "An Auto-Adaptive External Knee Prosthesis," Artificial Intelligence Laboratory, MIT, Sep. 2000, Cambridge, MA, pp. 1-3.
Wilkenfeld, A. J., "Biologically inspired auto adaptive control of a knee prosthesis," Ph.D, Thesis, Massachusetts Institute of Technology, Oct. 23, 2000.
Williamson, M., "Series Elastic Actuators," Artificial Intelligence Laboratory, MIT, Jan. 1995, Carnbridge, MA, pp. 1-74.
Wiliemsen A., et al., "Automatic Stance-Swing Phase Detection from Accelerometer Data for Peroneal Nerve Stimulation," IEEE Transactions on Human Factors in Electronics, vol. 37, No. 12, Dec. 1990, pp. 1201-1208.
Wiilemsen A., et al., "Real-Time Gait Assessment Utifizing a New Way of Accelerometry," Journal of Biomechanics, vol. 23, No. 8, 1990, pp. 859-863.
Williams, B., "Mode Estimation of Model-based Programs: Monitoring Systems with Complex Behavior," Proceedings of the International Joint Conference on Artificial Intelligence, Aug. 2001, Seattle, WA, pp. 1-7.
Winter, D. A, "Energy generation and absorption at the ankle and knee during fast, natural, and slow cadences," Clinical Orthopedics and Related Research, vol. 175, May 1983, pp. 147-154.
Winter, D, and Robertson D., "Joint torque and energy patterns in normal gait," Biol. Cybern., vol. 29, May 1978, pp. 137-142.
Winter, D. and Sienko S., "Biomechanics of below-knee amputee gait," Journal of Biomechanics, vol. 21, No. 5, Aug. 1986, pp. 361-367.

(56) References Cited

OTHER PUBLICATIONS

Wisse, M., "Essentials of Dynamic Walking, Analysis and Design of two-legged robots," Ph.D Thesis, Technical University of Delft, 2004, pp. 1-195.
Woodward et al., "Skeletal Accelerations measured during different Exercises," Proceedings of the Institution of Mechanical Engineers, Part H: Journal of Engineering in Medicine, vol. 207, Jun. 1993, pp. 79-85.
Wu, The Study of Kinematic Transients in Locomotion Using the Integrated Kinematic Sensor, IEEE Transactions or Rehabilitation Engineering, vol. 4, No. 3, Sep. 1996, p. 193-200.
Yakovenko, S., et. al., "Contribution of stretch reflexes to locomotor control: a modeling study," Bioi Cybern, vol. 90, No. 2, Jan. 2004, pp. 146-155.
Yun X., "Dynamic state feedback control of constrained robot manipulators," Proc. of the 27th conference on Decision and Control, Dec. 1988, pp. 622-626.
Ziatnik, D., et. al., "Finite-state control of a trans-femoral prosthesis," IEEE Trans. on Control System Technology, vol. 10, No. 3, May 2002, pp. 408-420.
Seibert, P., "MIT professor and double amputee invents the iwalk PowerFoot, the world's most advanced robotic prosthetic foot", Hub Tech Insider [online] Dec. 3, 2009 [retrieved on Aug. 14, 2019]. Retrieved from Interent URL: https://hubtechinsider.wordpress.com/2009/12/03/mit-professor-and-double-amputee-invents-the-iwalk-powerfoot-the-worlds-most-advanced-robotic-prosthetic-foot/, 14 pages.
Communication pursuant to Article 94(3) EPC for Application No. 12701403.3, dated Aug. 8, 2019, 8 pages.

\* cited by examiner

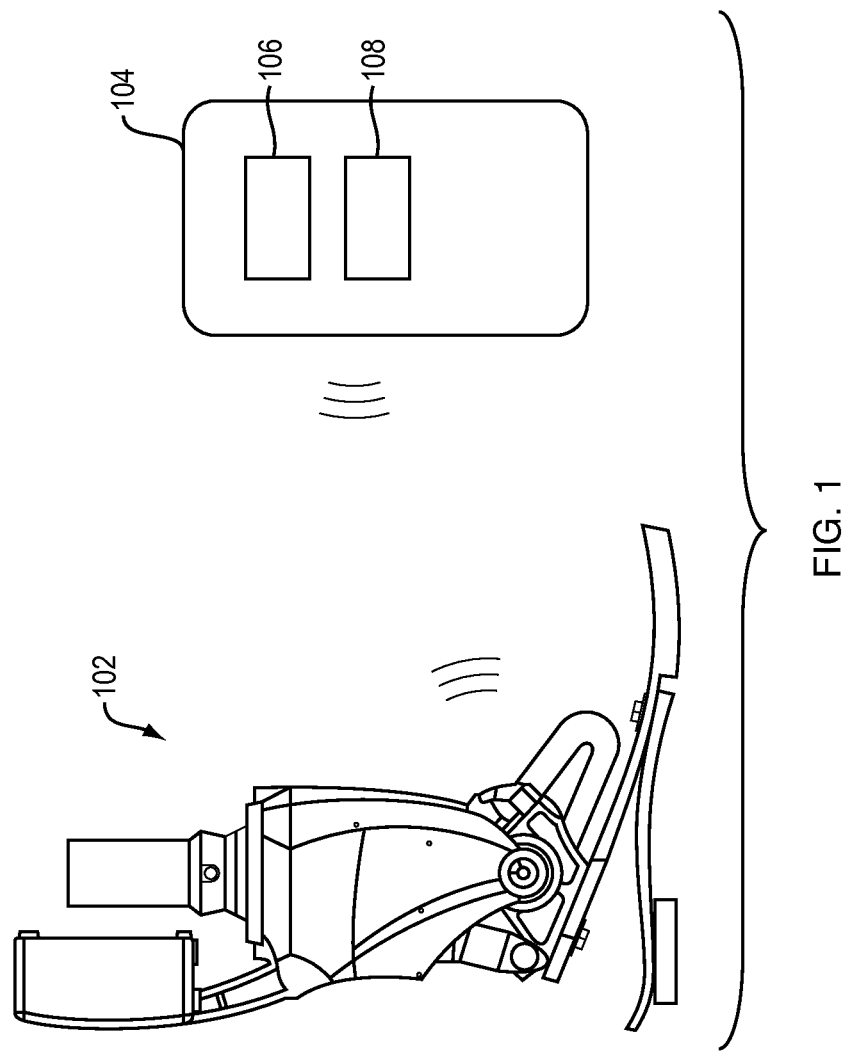

| PARAMETER OF A POWERED DEVICE | TYPICAL RANGE |
|---|---|
| WEIGHT | 100 TO 300, lb |
| EARLY STANCE STIFFNESS | 300 TO 1300 |
| EARLY STANCE DAMPING | 2 TO 50 |
| POWER COEFFICIENT (i.e., pff) | 50 TO 400 |
| TIMING EXPONENT | 3 TO 5 |
| SENSITIVITY OF HARD STOP | -150 TO 150, MILLI-DEGREE |
| THRESHOLD FOR LOW POWER MODE (CAFÉ MODE) | -320 TO 0, CENTI-RAD/s |
| SLOW WALK POWER COEFFICIENT | 0 TO 1 |
| STAIR WALK POWER COEFFICIENT | 0 TO 1.5 |

FIG. 4

CONTROLLING POWERED HUMAN AUGMENTATION DEVICES

RELATED APPLICATIONS

This application is a continuation of U.S. patent application Ser. No. 13/349,216, filed on Jan. 12, 2012, entitled "Controlling Powered Human Augmentation Devices" which claims priority to and the benefit of U.S. Provisional Patent Application Ser. No. 61/432,093, filed on Jan. 12, 2011, entitled "User Interface For Adjusting A Prosthesis Or Orthosis" the entire contents of each of which is hereby incorporated by reference in its entirety.

FIELD OF THE INVENTION

This invention relates generally to powered human augmentation devices, such as lower-extremity prosthetic orthotic, or exoskeleton apparatus, designed to emulate human biomechanics and to normalize function, components thereof, and methods for controlling the same.

BACKGROUND

Approximately 65% of service members seriously injured in Iraq and Afghanistan sustain injuries to their extremities. Many of these individuals experience muscle tissue loss and/or nerve injury, resulting in the loss of limb function or substantial reduction thereof. Injuries to the lower leg can be particularly devastating, due to the critical importance of the ankle in providing support for body position and in propelling the body forward economically during common functions, such as level-ground walking and the ascent and descent of stairs and slopes.

Increasingly, robotic technology is employed in the treatment of individuals suffering from physical disability, either for the advancement of therapy tools or as permanent assistive devices. An important class of robotic devices provides therapy to the arms of stroke patients. Additionally, lower-extremity robotic devices have been developed for the enhancement of locomotor function. Although decades of research has been conducted in the area of active permanent assistive devices for the treatment of lower-extremity pathology, many of these devices are not designed to produce a biomimetic response, generally described in terms of joint torque, joint angle, and other related parameters as observed in a human not having substantial muscle tissue injury and not using any device to assist in ambulation. Therefore, these robotic devices may cause discomfort to the wearer. The commercially available ankle-foot orthotic devices are generally passive, non-adaptive devices.

Some powered prosthetic and orthotic devices have been described in co-pending U.S. patent application Ser. No. 12/157,727 "Powered Ankle-Foot Prosthesis" filed on Jun. 12, 2008 (Publication No. US2011/0257764 A1); co-pending U.S. patent application Ser. No. 12/552,013 "Hybrid Terrain-Adaptive Lower-Extremity Systems" filed on Sep. 1, 2009 (Publication No. US2010/0179668 A1); co-pending U.S. patent application Ser. No. 13/079,564 "Controlling Power in a Prosthesis or Orthosis Based on Predicted Walking Speed or Surrogate for Same" filed on Apr. 4, 2011; co-pending U.S. patent application Ser. No. 13/079,571 "Controlling Torque in a Prosthesis or Orthosis Based on a Deflection of Series Elastic Element" filed on Apr. 4, 2011; and co-pending U.S. patent application Ser. No. 13/347,443 "Powered Joint Orthosis" filed on Jan. 10, 2012. These powered devices are adopted to provide at least a biomimetic response and can eliminate or mitigate slapping of the foot after heel strike (foot slap) and dragging of the toe during swing (toe drag). In general, a biomimetic response refers to a range of responses from humans and can vary according to the wearer of the powered device and the nature and environment of the wearer's activity. As such, even the powered devices described above need to be tailored or calibrated to the wearer so as to reliably provide a biomimetic response. Therefore, there is a need for systems and methods of controlling permanent assistive devices for the treatment of lower-extremity pathology to achieve optimal wearer comfort and satisfaction.

SUMMARY

In various embodiments, the present invention provides systems and methods that can dynamically control a powered prosthetic/orthotic human augmentation device, such that the device can provide and maintain at least a biomimetic response during the wearer's activity. This is achieved, in part, by recording within a gait cycle typical ranges of various ambulation-related parameters in humans not having substantial muscle tissue injury and not using any device to assist in ambulation. A user interface is provided that enables an operator, the wearer, or another person to adjust various parameters of the powered device such that the response of the powered device, as described in terms of the ambulation-related parameters, is substantially similar to the recorded ranges of those parameters, i.e., at least biomimetic. These adjustments may be carried out in a training mode, during actual use, or both. The parameters of the powered device may also be adjusted or modified according to the wearer's characteristics, such as weight, desired walking speed, etc. and/or according to ambulation patterns, such as slow walking, walking in incomplete steps or shuffling, etc. Moreover, the parameters of the powered device may also be adjusted or modified according to terrain and activity, e.g., walking upslope, downslope, ascending and/or descending stairs, etc. Accordingly, a biomimetic response of the powered prosthetic/orthotic device can be maintained throughout the duration of the wearer's activity, regardless of terrain, walking speed, etc.

In one aspect, embodiments of the invention feature a method of controlling a powered human augmentation device. The method includes adjusting a parameter of the powered device within a gait cycle by wirelessly transmitting a control signal thereto. After adjustment based on the control signal, the adjusted parameter falls within a target range corresponding to that parameter, providing at least a biomimetic response to a wearer of the powered device. The parameter may be net work, toe-off angle, peak power applied by the powered device, or timing of the peak power relative to the gait cycle. In some embodiments, more than one or even all of these parameters are adjusted. The target range corresponding to the parameter may be a function of ambulation speed and/or ambulation pattern. The adjusting step may also be based, at least in part, on one or more of the ambulation speed, ambulation pattern, terrain, and activity. The activity may include walking on level ground, walking on uneven ground, walking upslope, walking downslope, ascending stairs, and/or descending stairs.

In some embodiments, the adjusting step is related to one or more of weight of the wearer, early-stance stiffness, power applied by the powered device, timing of application of power, hard-stop sensitivity, and a speed threshold for low-power mode of the powered device. The adjusted parameter may also include a gain in a positive force-feedback control loop that can adjust the power applied by the powered device and/or an exponent in a positive force-feedback that can adjust the timing of the application of power.

In some embodiments, the method includes the step of receiving a data signal from the powered device, such that adjusting the parameter is based at least in part on the received data signal. The received data signal may be related to one or more of rate of plantar flexion, heel rise, and ambulation-step length. The control signal may be transmitted during a training mode, a use mode, or both. The method may also include the step of storing the transmitted control signal for subsequent retransmission thereof.

In another aspect, a communication system for interfacing with a powered human augmentation device includes a wireless transmitter for adjusting a parameter of the powered device. The parameter is adjusted within a gait cycle by transmitting a control signal to the powered device, such that the adjusted parameter falls within a target range corresponding to that parameter. This provides at least a biomimetic response to a wearer of the powered device.

The parameter may be net work, toe-off angle, peak power applied by the powered device, or timing of the peak power relative to the gait cycle. In some embodiments, more than one or even all of these parameters are adjusted. The target range corresponding to the parameter may be a function of ambulation speed and/or ambulation pattern. The adjustment of the parameter may also be based, at least in part, on one or more of the ambulation speed, ambulation pattern, terrain, and activity. The activity may include walking on level ground, walking on uneven ground, walking upslope, walking downslope, ascending stairs, and/or descending stairs.

In some embodiments, the parameter adjustment is related to one or more of weight of the wearer, early-stance stiffness, power applied by the powered device, timing of application of power, hard-stop sensitivity, and a speed threshold for low-power mode of the powered device. The adjusted parameter may also include a gain in a positive force-feedback control loop that can adjust the power applied by the powered device and/or an exponent in a positive force-feedback that can adjust the timing of the application of power.

In some embodiments, the communication system includes a receiver for receiving a data signal from the powered device, such that adjusting the parameter is based at least in part on the received data signal. The received data signal may be related to one or more of rate of plantar flexion, heel rise, and ambulation-step length. The control signal may be transmitted during a training mode, a use mode, or both. The communication may also store the transmitted control signal for subsequent retransmission thereof.

The powered augmentation device may be a prosthetic device or an orthotic device, such as an exoskeleton. In some embodiments, the wireless transmitter is adapted to transmit the control signal to a second powered human augmentation device. The wireless transmitter may include a transmitter of a mobile device, and the mobile device can be a cell phone, a personal digital assistant, or a tablet PC.

In yet another aspect, various embodiments feature an article of manufacture, including a non-transitory machine-readable medium storing instructions. The instructions, when executed by a processor, configure the processor to adjust a parameter of the powered device within a gait cycle by wirelessly transmitting a control signal thereto. After adjustment based on the control signal, the adjusted parameter falls within a target range corresponding to that parameter, providing at least a biomimetic response to a wearer of the powered device.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations. As used herein, the term "substantially" means±10% and, in some embodiments, ±5%.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 1 depicts an exemplary prosthetic device and a communication system according to one embodiment;

FIG. 4 shows various parameters of a powered device that may be adjusted, and the ranges of those parameters, according to one embodiment.

DESCRIPTION

Figure 2A:
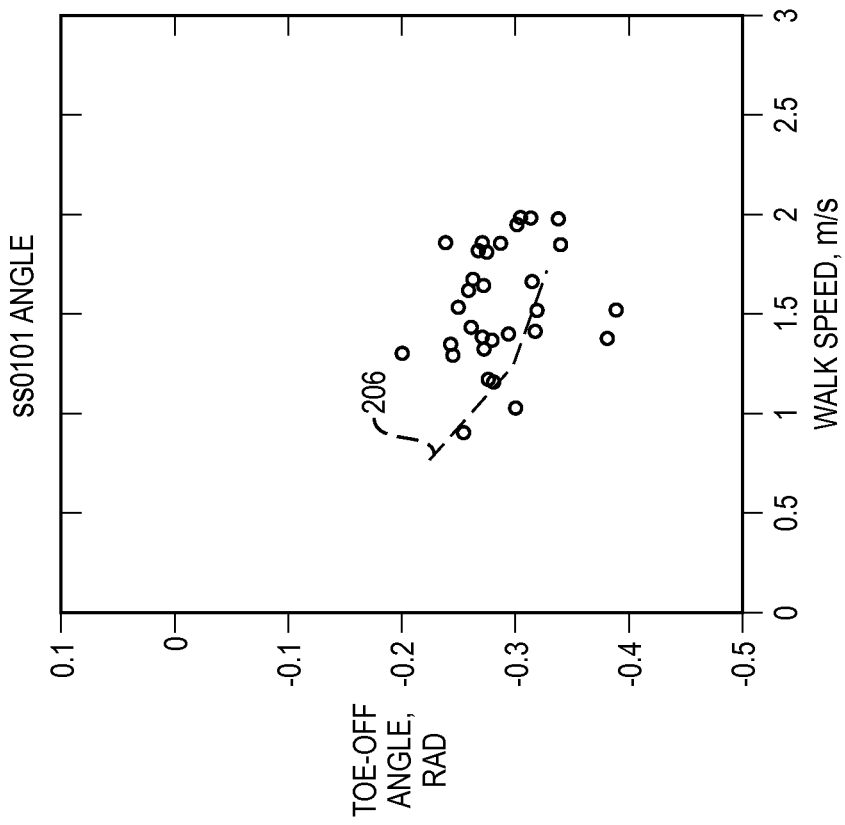
FIGS. 2a-2d depict various joint parameters within a gait cycle, describing respective biomimetic responses.

The entire contents of each of U.S. patent application Ser. No. 12/157,727 "Powered Ankle-Foot Prosthesis" filed on Jun. 12, 2008 (Publication No. US2011/0257764 A1); U.S. patent application Ser. No. 12/552,013 "Hybrid Terrain-Adaptive Lower-Extremity Systems" filed on Sep. 1, 2009 (Publication No. US2010/0179668 A1); U.S. patent application Ser. No. 13/079,564 "Controlling Power in a Prosthesis or Orthosis Based on Predicted Walking Speed or Surrogate for Same" filed on Apr. 4, 2011; U.S. patent application Ser. No. 13/079,571 "Controlling Torque in a Prosthesis or Orthosis Based on a Deflection of Series Elastic Element" filed on Apr. 4, 2011; and U.S. patent application Ser. No. 13/347,443 "Powered Joint Orthosis" filed on Jan. 10, 2012 are incorporated herein by reference.

FIG. 1 shows a BiOM™ Ankle 102, a powered prosthetic ankle available from iWalk, Inc. (Bedford, Mass.), and a smart phone 104 for controlling/tuning various parameters of the BiOM Ankle 102. The smart phone 104 includes a transmitter 106 for sending one or more control signals to the BiOM Ankle 102, whereby one or more parameters of the BiOM Ankle 102 can be adjusted. The smart phone 104 also includes a receiver 108 for receiving parameter values as data signals from the BiOM Ankle 102 which has a corresponding transmitter and receiver capability. These data signals can be used to adjust the values of the corresponding and/or other parameters of the BiOM Ankle 102. To facilitate convenient adjustment of various parameters, the BiOM Ankle 102 provides a user interface that includes a software application and firmware. The software application, implemented in Java for the Android 2.1 Operating System, may be run on the smart phone 104. The software application builds a packet structure that is sent out over Android's Bluetooth hardware interface. Corresponding software on the BiOM Ankle 102, written in C and stored in the firmware of the BiOM Ankle 102, receives commands from the same packet structure, and adjusts the operation of the BiOM Ankle 102 accordingly.

It should be understood that the BiOM Ankle 102 and the smart phone 104 are illustrative only and, in general, a powered human augmentation device can be any powered prosthetic, orthotic and/or exoskeleton device that can assist in ankle, knee, and/or hip function. Uses in other joint devices are also contemplated. The communication system, in general, can be any mobile communication device capable of communicating with the powered device. Exemplary mobile communication devices include smart phones, personal digital assistants (PDAs, such as a BlackBerry), tablet computers, etc. The communication between the communication system and the powered device may be established via wireless link such as Bluetooth, WiFi, etc., or via a wired link. The software applications run on the BiOM Ankle 102 and the smart phone 104 may also be written in any other programming languages and/or may be provided as circuitry.

Various parameters of the BiOM Ankle 102 (or in any powered human augmentation device, in general) are controlled using the smart phone 104, such that the BiOM Ankle 102 produces at least a biomimetic response. Such a response may enable a wearer of the powered device to ambulate in a natural manner, e.g., in a manner in which a typical human not using a powered device walks (i.e., slowly or briskly), ascends/descends stairs, etc. In addition to enabling ambulation with a natural feel, a powered device producing at least a biomimetic response can also decrease stress on other body parts of the human, e.g., on knees and hips while using the BiOM Ankle 102. As a result, net metabolic cost of transport to the wearer can be minimized.

In one embodiment, a biomimetic response of a human can be characterized by four parameters, namely, net work, toe-off angle, peak power, and peak-power timing. Each of these parameters varies according to the human's ambulation speed. Net work is the time integral of mechanical power applied by the powered device (e.g., the BiOM Ankle 102) during one ambulation step (i.e., gait cycle). FIG. 2a shows that for typical humans, who do not have injured muscle tissue and do not use a powered augmentation device, the net work normalized according to the human's weight varies according to the walking speed, but stays within a certain range. For example, at a walking speed of about 1.5 m/s, the normalized net work may be in the range of about 0.1-0.25 J/kg, and at a walking speed of about 2 m/s the normalized net work may be in the range of about 0.2-0.4 J/kg.

A net-work response of a powered augmentation device is biomimetic if the net work produced by the device remains within a range corresponding to the ambulation speed, i.e., substantially within the dashed lines 202, 204. If the net-work response of the powered device falls outside the range indicated by the lines 202, 204, one or more parameters of the device can be tuned using the communication system, e.g., the smart phone 104, (as described below), such that the net work is adjusted to fall within a desired range.

Figure 2B:
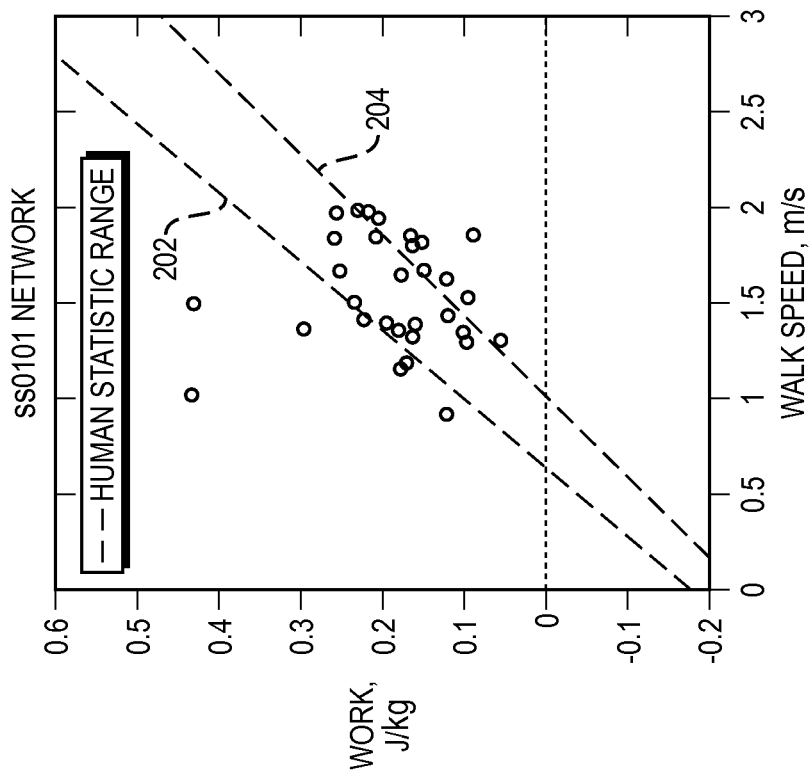

FIG. 2b depicts a relationship between the toe-off angle and walking speed for a typical human. If the toe-off angle while using a powered augmentation device is not substantially the same as that indicated by the dashed line 206, the foot may not be plantarflexing sufficiently. Therefore, one or more parameters of the powered device (e.g., BiOM Ankle 102) may be tuned using the smart phone 104.

Figure 2D:
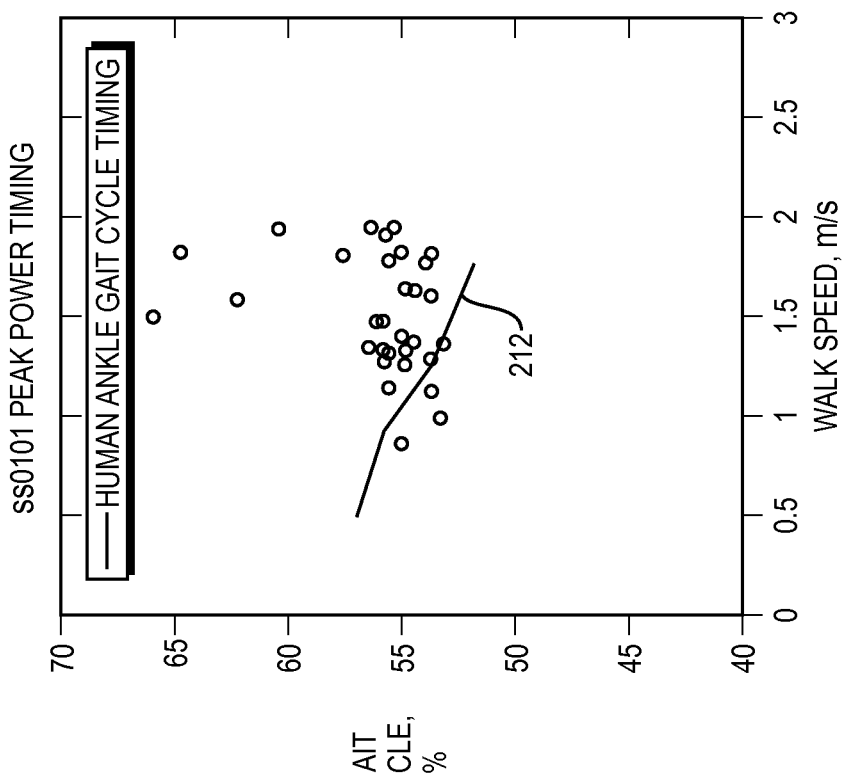
Figure 2C:
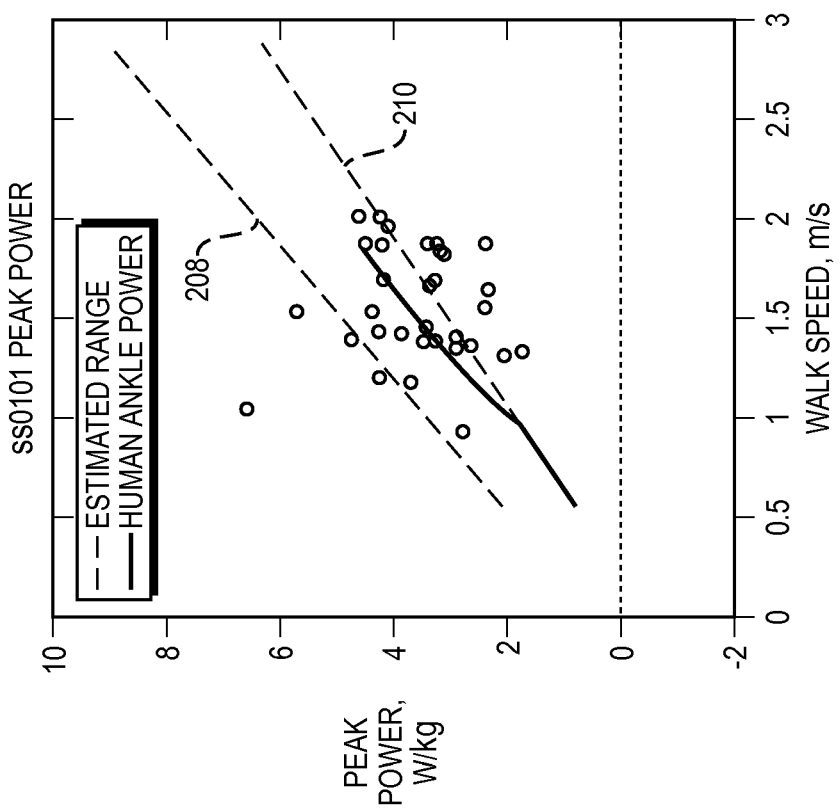
Figure 3A:
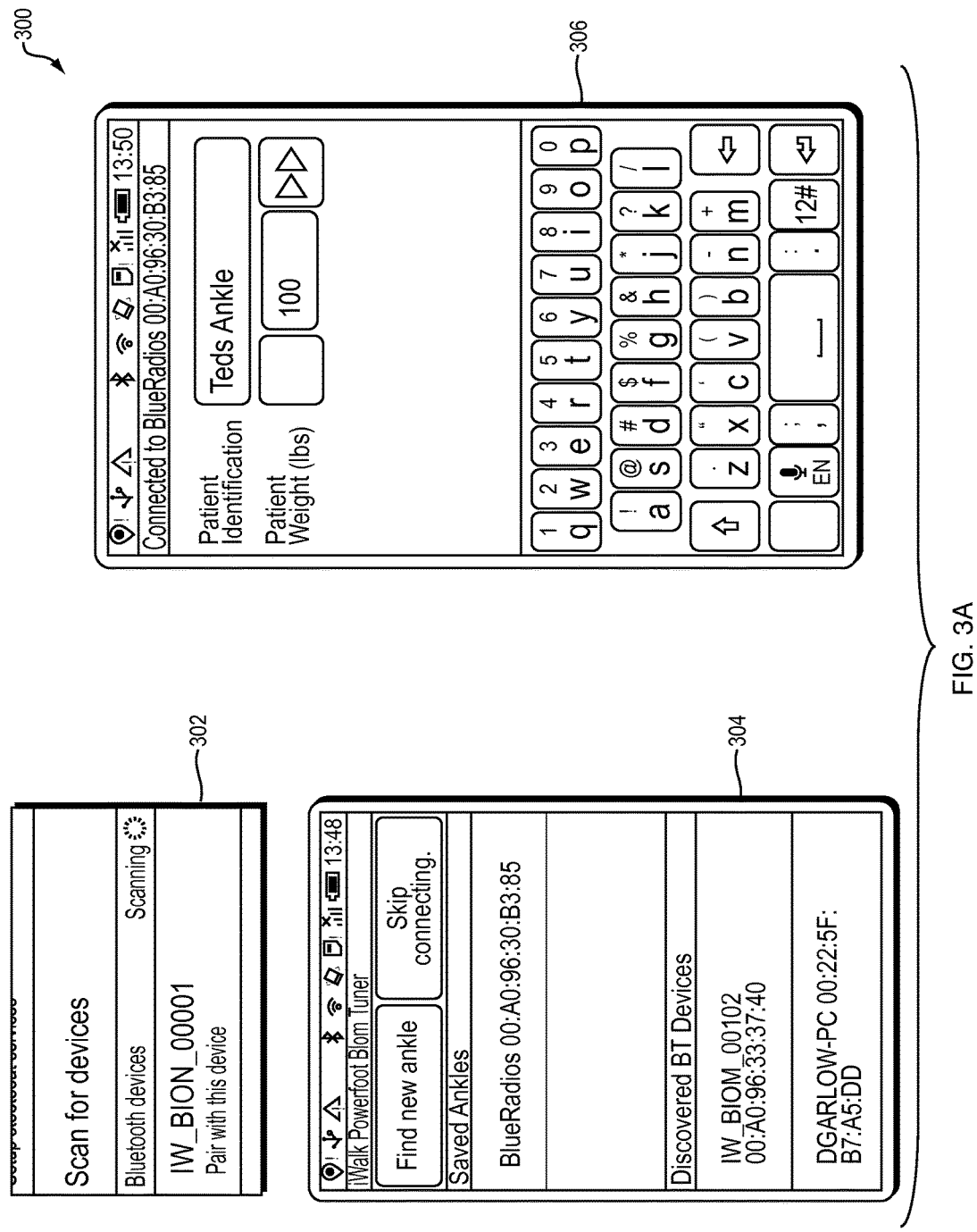
FIGS. 3a-3e depict steps of adjusting various parameters of a powered device according to one embodiment.
Figure 3B:
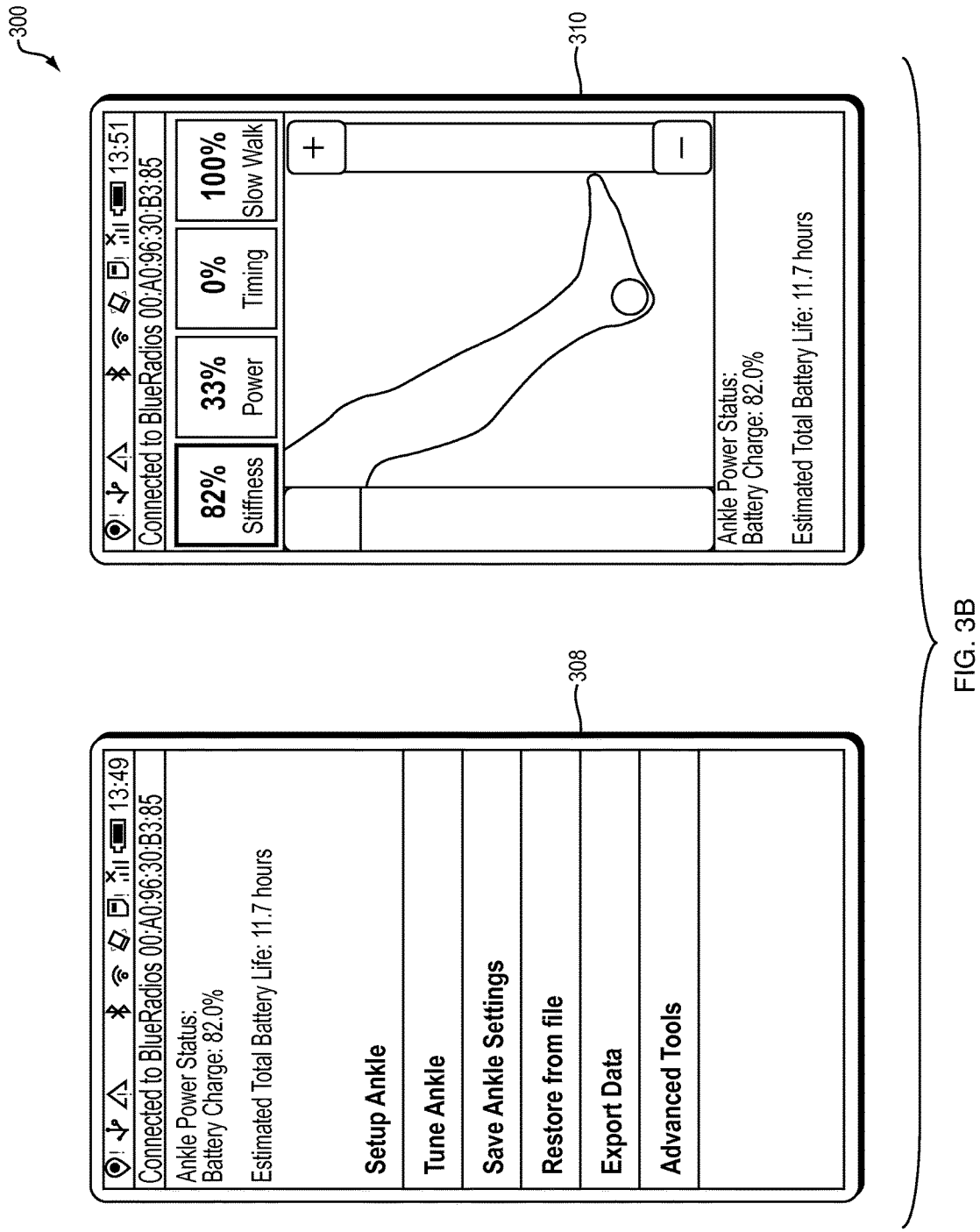
Figure 3C:
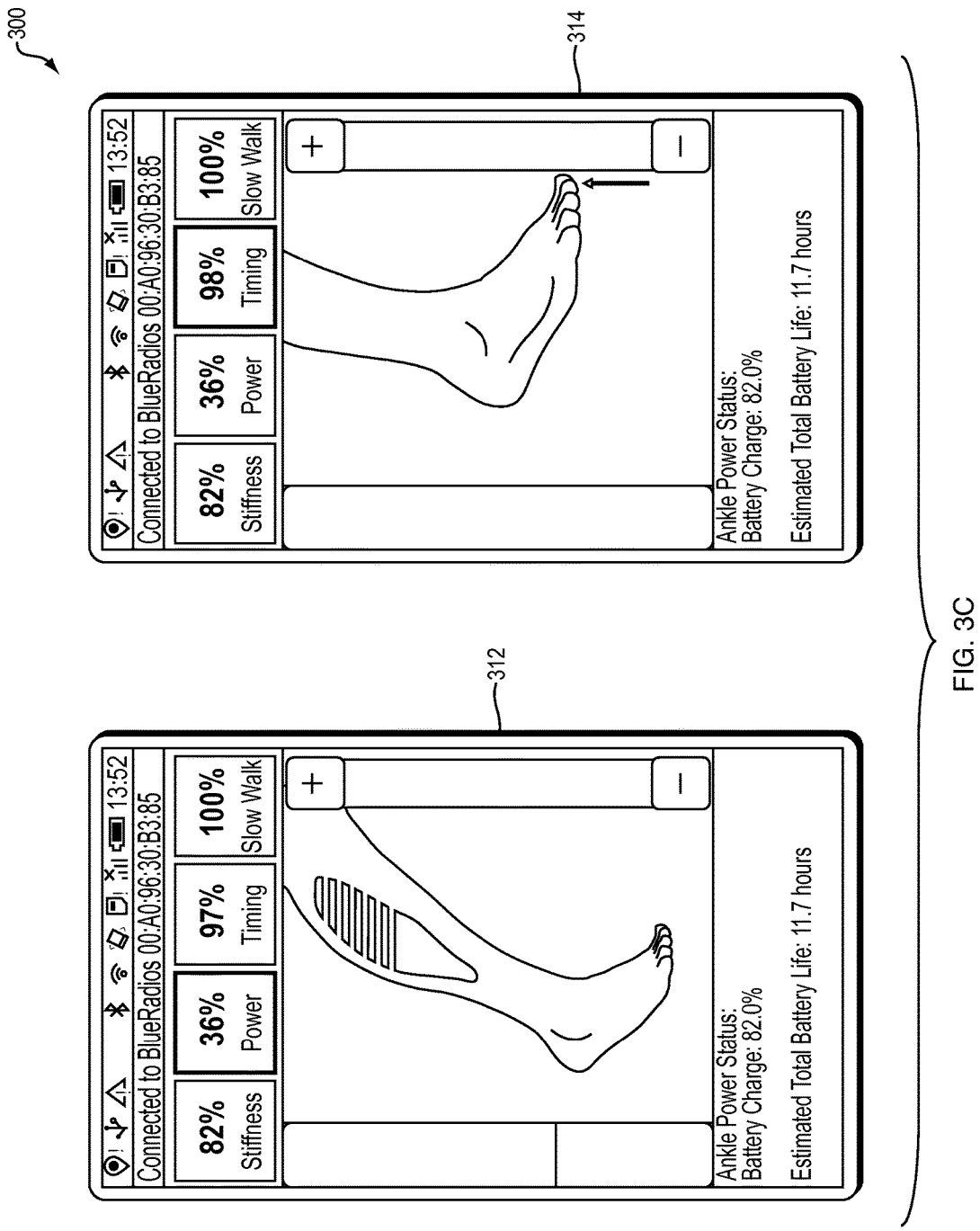
Figure 3D:
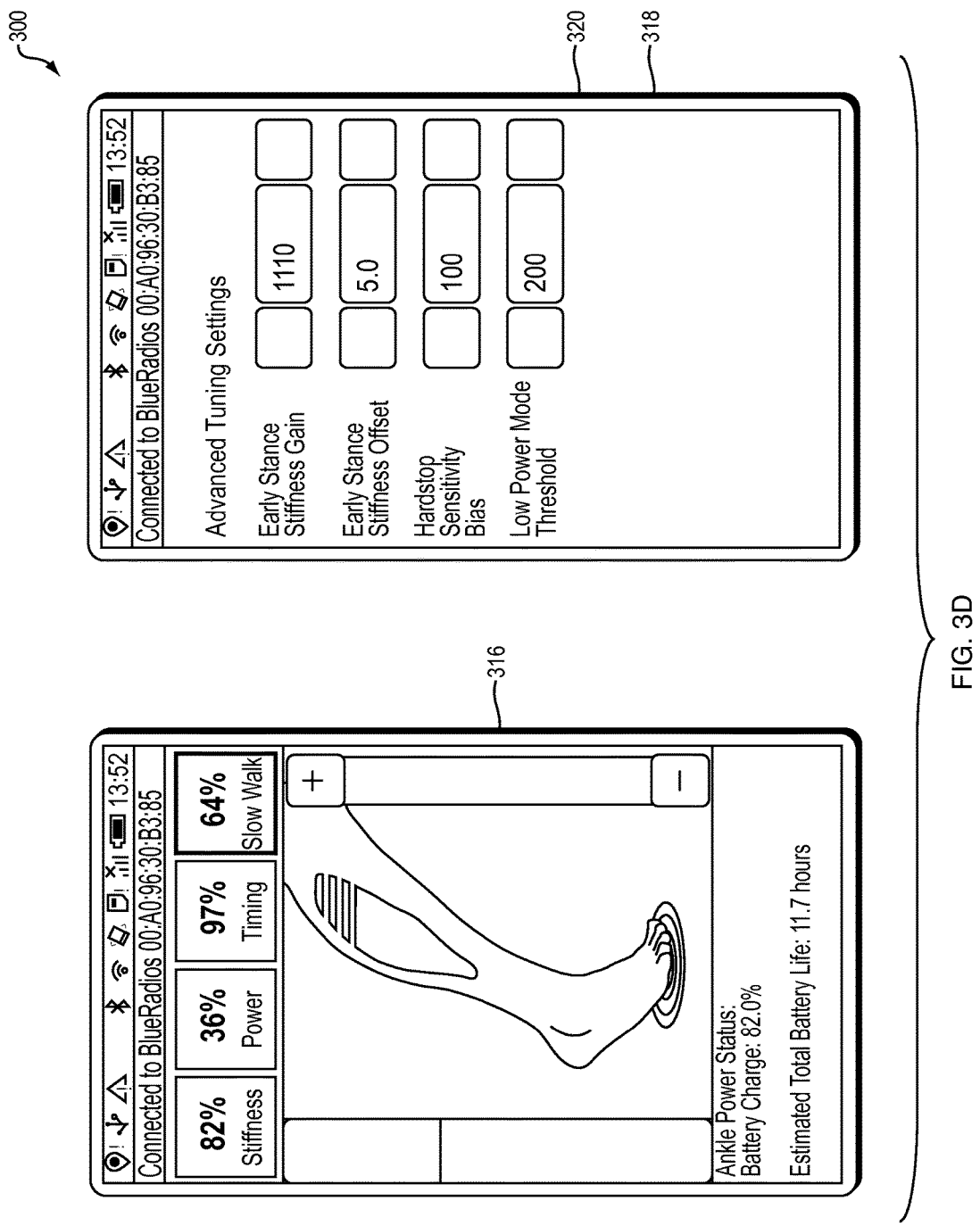
Figure 3E:
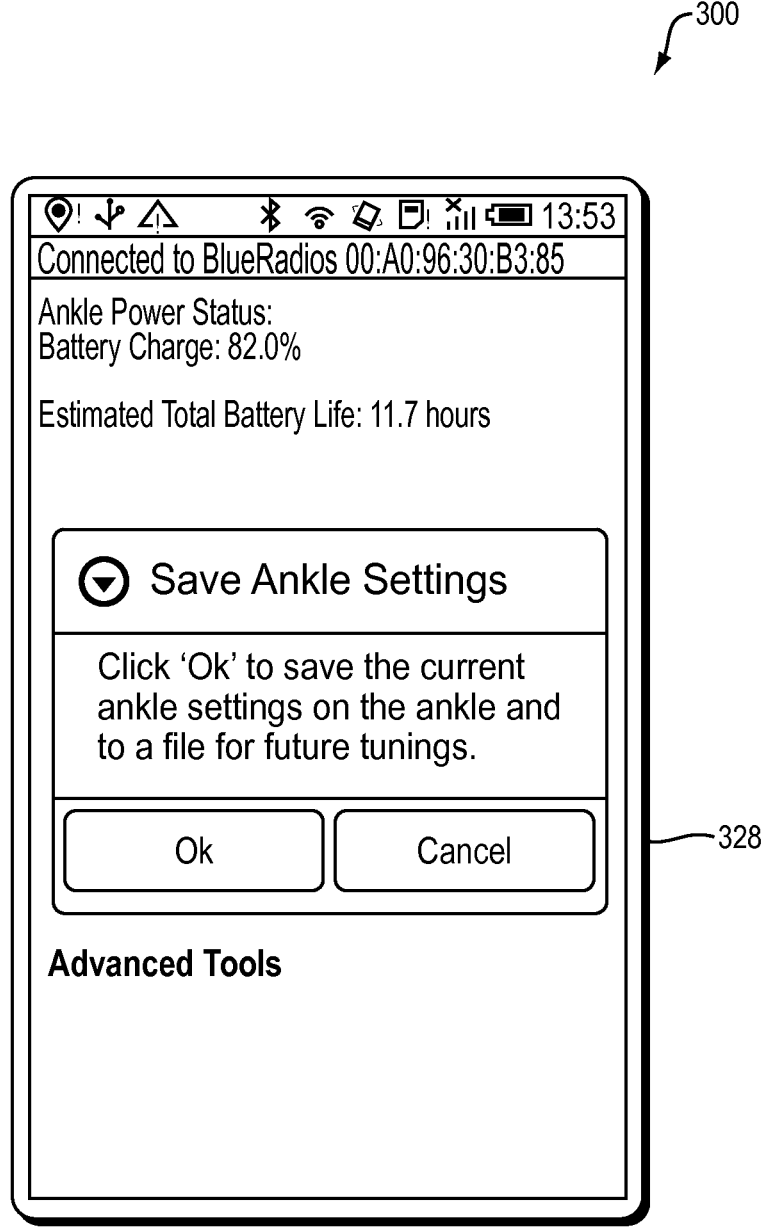

FIGS. 2c and 2d depict the peak power delivered by a typical human and timing within a gait cycle at which the peak power is delivered, respectively. If the peak power to the ankle (a joint, in general) delivered by a powered augmentation device does not fall within the range indicated by the dashed lines 208, 210, the wearer receives too little or too much power. If the powered augmentation device delivers the peak power at a time less than that indicated by line 212, the peak power may be delivered too early, i.e., significantly before the time at which the powered plantar flexion state of the gait cycle begins. In this case, the wearer might feel that the ankle is lifting up but not pushing/propelling forward sufficiently. On the other hand, if the powered augmentation device delivers the peak power at a time substantially greater than that indicated by the line 212, the peak power may be delivered too late, i.e., significantly after the time at which the powered plantar flexion state of the gait cycle begins. In this case, the wearer might feel that the ankle is pushing forward but not lifting up sufficiently.

In any of the scenarios describe above, unlike a typical human, the wearer may not receive adequate power to the ankle at the time of toe off, resulting in unnatural ambulation. Therefore, one or more parameters of the powered device may be adjusted such that at a certain ambulation speed the peak power applied by the device remains substantially within the range indicated by the dashed lines 208, 210. Moreover, one or more parameters may also be adjusted such that the timing within the gait cycle at which the powered device delivers the peak power corresponds generally to that indicated by the line 212.

In general, by tuning one or more parameters of the powered augmentation device using a communication system, each of the net work, toe-off angle, peak power, and peak power timing can be adjusted, such that the powered device delivers at least a biomimetic response to the wearer. In some instances, the parameters such as the peak power and peak power timing can be adjusted directly. In other instances, other related parameters, e.g., heel stiffness, are adjusted using the communication system, which in turn causes an adjustment of the parameters described with reference to FIGS. 2a-2d.

With reference to FIGS. 3a-3e, in an exemplary tuning process 300, a communication system (phone for convenience, hereafter) scans for a powered augmentation device within the phone's range, in step 302. When any such devices are located, one of them may be selected and a Bluetooth connection is established with that device in step 304, pairing the phone with the selected powered device. In general, the phone can be paired with more then one powered devices. In step 306, the wearer's ID and weight are entered and the transmitter of the phone may supply the weight to the paired power device by sending a control signal thereto. The wearer's weight may range from about 100 lbs up to about 300 lbs. Various parameters of the powered device adjusted subsequently may be adjusted according to the wearer's weight.

In step 308, a powered ankle device is tuned by selecting "Tune Ankle." In other embodiments, other joints such as knee or hip may be tuned alternatively or in addition. In step 310, the wearer walks at a self-selected walking speed (SSWS), and an operator i.e., the wearer himself/herself or another person (clinician, researcher, etc.) adjusts "stiffness," e.g., by gradually increasing it from zero. In response, the rate of plantar flexion may change, which is observed by the operator, or the wearer may inform it to the operator. In some embodiments, a sensor of the powered device may sense the rate of plantar flexion and may transmit a corresponding data signal to the phone. The phone may then display the sensed rate to the operator. In the step 308, the operator adjusts the stiffness so as to achieve a desired rate of plantar flexion which, in turn, adjusts one or more of the net work, toe-off angle, peak power, and peak power timing.

In step 312, the power applied by the powered augmentation device is adjusted by asking the wearer to walk at SSWS. The operator gradually increases the power from an initial value (e.g., zero percent) until the wearer verifies that powered plantar flexion is engaged correctly, i.e., adequate power is received approximately at the time the ankle dorsiflexion is at a maximum level. Increasing (decreasing) the power may include increasing (decreasing) a gain parameter in a positive-feedback system of the powered device that delivers the power. In some embodiments, correct engagement of the powered plantar flexion can be verified by analyzing various sensors signals detected by the powered augmentation device and transmitted to the communication system as data signals. The received data signals may relate to parameters such as heel rise, walking-step length, and tracking performed during the swing phase. The operator may also manually (e.g., visually) compare values of these parameters with their values corresponding to a previous power setting, so as to identify the power setting that results in at least a biomimetic response as described above and/or the wearer's preference.

The timing at which peak power is applied by the powered augmentation device (e.g., the BiOM Ankle 102 shown in FIG. 1) is adjusted in step 314 by asking the wearer to walk at SSWS. The operator adjusts the "Power Trigger" timing such that power is delivered at terminal stance, i.e., approximately at the time the ankle dorsiflexion is at a maximum level. Adjusting the power timing may include adjusting an exponent parameter in a positive-feedback system that delivers the power. Whether the timing is correct may be verified by the wearer. The operator may also verify that gait cycle is balanced and that a desired knee flexion is maintained during stance. Alternatively, or in addition, data signals corresponding to various parameters of the powered device may be received therefrom, and used to guide adjustment of the power trigger. Adjusting the timing of application peak power enables timely powered plantar flexion at toe off. This adjustment can also allow the wearer to take a full step using the leg having any injured muscle tissue.

When a wearer prefers to walk at a speed slower than the SSWS, the parameters of the powered device may be readjusted, to provide a biomimetic response corresponding to the slower speed, in part, and also to conserve battery life, in part. To this end, in step 316, the wearer is asked to walk at a slower speed, and the power is adjusted down from an initial value (e.g., 100%) which may be the power setting for the SSWS, to a "slow-walk mode" setting. The power may be adjusted according to the wearer's preference and/or according to parameters such as heel rise, walking-step length, and tracking performed during the swing phase. The values of these parameters may be received from the powered device as data signals and/or may be observed by the operator similarly as described in the step 310.

The slow-walk mode can also be used to adjust parameters according to the wearer's ambulation pattern, e.g., when the wearer does not take full steps or shuffles. In the step 318, a threshold at which the BiOM Ankle's slow-walk mode, also called "low-power" mode engages can also be adjusted. In addition to conserving battery life, the slow-walk mode setting can increase walking efficiency at a slower speed and can also enhance the real-time response of the ankle.

In step 320, the hard-stop sensitivity of the powered device can be adjusted. The hard stop corresponds to the wearer's walking speed, and the maximum dorsiflexion angle embodied within the design of the powered device. Generally, the small angular displacements that occur after engagement of the hard-stop are used to estimate ankle torque. This torque is an important input to the positive force feedback. By slightly changing this torque model parameter, an increased or decreased reflex torque adjustment can be made which is particularly useful for slow walking performance. The hard-stop sensitivity can be increased such that the powered device delivers more power (e.g., compared to the power setting for the SSWS) early in the gait cycle, and the hard-stop sensitivity can be decreased such that relatively less power is delivered later in the gait cycle.

The communication device can also facilitate adapting the powered device to terrain and/or the wearer's activity. For example, power and/or timing of peak power can be adjusted to provide additional power when the wearer is walking upslope. These adjustment can be made as described with reference to the steps 312, 314. If the wearer is walking downslope, these parameters can be adjusted to provide adequate plantar flexion and knee stability when the foot rests flat on a surface. The phone (the communication system, in general) can set the powered device to operate in "Stair Mode." In this mode, the wearer is asked to ascend stairs, landing on the toe of a leg having affected muscle tissue. Various device parameters may be adjusted as described above with reference to the steps (power applied, in particular, as described in step 312) so that the powered augmentation device delivers at least a biomimetic response. The wearer may also be asked to descend stairs and the device parameters may be adjusted for descending stairs.

In step 328, the various device parameters adjusted in any of these steps can be saved for subsequent use. The tuning/adjusting described above may be performed in a training mode in one or more training sessions. More than one sets of settings, each set corresponding to one training session, may be saved for each joint (ankle, knee, hip, etc.), and may be restored during a subsequent use. The tuning/adjusting described above may also be performed during actual use of the powered device.

The ranges of various parameters described above with reference to FIGS. 3*a*-3*e* according to one embodiment are shown in a Table in FIG. 4. The Table shows additional parameters of the powered device that may be adjusted, so as to achieve and maintain at least a biomimetic response, and typical ranges of those parameters. It should be understood that the parameters shown in the Table are illustrative, and that according to some embodiments fewer or additional parameters may be controlled. Some other embodiments may control different parameters, and/or the typical ranges within which the parameters can be set may be different.

Accordingly, various embodiments of the invention may be used to initially set up or tune an augmentation device at the time of manufacture and commissioning to achieve a biomimetic response, on an individual employed as a model for this purpose. The device can then be fitted to the end user and the device further adjusted to tailor the device to that individual. As described, achieving a biomimetic response is a primary objective, in order to order to normalize user function and satisfaction. However, the methods and systems according to various embodiments of the invention may be used to achieve a greater than biomimetic response, or vary one or more of the response parameters as desired by the user or the user's physician, therapist, or clinician. Naturally, as will be understood, changes in a user's weight, strength, endurance or other physical condition may require further monitoring and adjustment of the device over time. Accordingly, the systems and associated methods may be utilized on regular time intervals or whenever a change to user or device occurs that warrants checking.

While the invention has been particularly shown and described with reference to specific embodiments, it will be understood by those skilled in the art that various changes in form and detail may be made therein without departing from the spirit and scope of the invention as defined by the appended claims. The scope of the invention is thus indicated by the appended claims and all changes that come within the meaning and range of equivalency of the claims are therefore intended to be embraced.

What is claimed is:

1. A powered human augmentation ankle device comprising:
    a sensor configured to sense a rate of plantar flexion of the powered human augmentation ankle device;
    a wireless communication device configured to transmit, from the powered human augmentation device, the sensed rate of plantar flexion and to receive, at the powered human augmentation device, a control signal configured to cause the powered human augmentation ankle device to adjust at least one parameter of the powered human augmentation ankle device, the at least one parameter comprising a timing of an application of a peak power;
    wherein the adjustment of the timing of the peak power application occurs during a terminal stance of the gait cycle, and the powered human augmentation ankle device has a net work that is a function of the peak power over time;
    and a processor configured to execute instructions causing the processor to:
    establish communication between the powered human augmentation ankle device and a communication system,
    receive the sensed rate of plantar flexion from the sensor,
    transmit the sensed rate of plantar flexion using the wireless communication device,
    receive a control signal in response to the transmitting of the sensed rate of plantar flexion, the control signal comprising an instruction to adjust a heel stiffness related to the parameter of the powered human augmentation ankle device,
    and adjusting the heel stiffness based on the control signal, the adjusted heel stiffness causing the powered human augmentation ankle device to provide a biomimetic response having the net work over the gait cycle and the adjustment to the peak power timing,
    wherein the net work falls substantially within a target range that is a function of ambulation speed.

2. The system of claim 1, the net work further being a function of ambulation pattern.

3. The system of claim 1, wherein adjusting the parameter is based at least in part on ambulation pattern.

4. The system of claim 1, wherein adjusting the parameter is based at least in part on at least one of terrain or activity.

5. The system of claim 4, wherein the activity is selected from the group consisting of walking on level ground, walking on uneven ground, walking upslope, walking downslope, ascending stairs, or descending stairs.

6. The system of claim 1, wherein adjusting the parameter is further related to at least one of weight of the wearer, power applied by the powered device, or hard-stop sensitivity.

7. The system of claim 1, wherein the control signal is transmitted during at least one of a training mode or a use mode.

8. The system of claim 1, wherein the communication system is adapted to store the transmitted control signal for subsequent retransmission thereof.

9. The system of claim 1, wherein the powered augmentation ankle device is selected from the group consisting of a prosthetic device and an orthotic device.

10. The system of claim 1, wherein the communication system is adapted to transmit the control signal to a second powered human augmentation device.

11. The system of claim 1, wherein the communication system comprises a transmitter of a mobile device.

12. The system of claim 11, wherein the mobile device is selected from the group consisting of a cell phone, a personal digital assistance, a table, and a persona computer.

13. The system of claim 1, wherein the parameter is adapted to be adjusted manually by an operator.

14. The system of claim 13, wherein the parameter is adapted to be adjusted based on manual verification of the biomimetic response of the powered device.

15. The system of claim 1, the target range to be 0.1 to 0.25 J/kg for an ambulation speed of 1.5 m/s and 0.2 to 0.4 J/kg for an ambulation speed of 2.0 m/s.

* * * * *

UNITED STATES PATENT AND TRADEMARK OFFICE
CERTIFICATE OF CORRECTION

PATENT NO. : 10,537,449 B2
APPLICATION NO. : 14/090359
DATED : January 21, 2020
INVENTOR(S) : Zhixiu Han et al.

It is certified that error appears in the above-identified patent and that said Letters Patent is hereby corrected as shown below:

In the Claims

In Column 10, Line 39, please remove "assistance" and insert --assistant--

In Column 10, Line 39, please remove "table" and insert --tablet--

In Column 10, Line 39, please remove "persona" and insert --personal--

Signed and Sealed this
Fourteenth Day of April, 2020

Andrei Iancu
*Director of the United States Patent and Trademark Office*